US010894107B2

(12) United States Patent
Grinstead et al.

(10) Patent No.: US 10,894,107 B2
(45) Date of Patent: Jan. 19, 2021

(54) FOGGING SYSTEM PROVIDING ATOMIZED SOLUTION AND ULTRAVIOLET LIGHT TO TREATMENT AREA

(71) Applicant: GCMG COMPANIES, LLC, Oviedo, FL (US)

(72) Inventors: Steve Grinstead, Oviedo, FL (US); Frances Grinstead, Oviedo, FL (US)

(73) Assignee: GCMG COMPANIES, LLC, Oviedo, FL (US)

( * ) Notice: Subject to any disclaimer, the term of this patent is extended or adjusted under 35 U.S.C. 154(b) by 165 days.

(21) Appl. No.: 15/981,125

(22) Filed: May 16, 2018

(65) Prior Publication Data

US 2018/0353631 A1 Dec. 13, 2018

Related U.S. Application Data

(63) Continuation-in-part of application No. 15/658,803, filed on Jul. 25, 2017, now Pat. No. 10,092,668, (Continued)

(51) Int. Cl.
*A61L 9/00* (2006.01)
*A61L 2/00* (2006.01)
(Continued)

(52) U.S. Cl.
CPC ............... *A61L 2/208* (2013.01); *A61L 2/10* (2013.01); *A61L 2/183* (2013.01); *A61L 2/22* (2013.01);
(Continued)

(58) Field of Classification Search
CPC ... A61L 9/00; A61L 9/015; A61L 2/22; A61L 2/24; A61L 9/14
(Continued)

(56) References Cited

U.S. PATENT DOCUMENTS 4,366,125 A 12/1982 Kodera et al.
7,604,774 B2 * 10/2009 Mole .................. A61L 2/24
422/28
(Continued)

FOREIGN PATENT DOCUMENTS

JP H1057749 3/1998

OTHER PUBLICATIONS

Utility U.S. Appl. No. 16/207,525, filed Dec. 3, 2018 (Grinstead).
(Continued)

*Primary Examiner* — Monzer R Chorbaji
(74) *Attorney, Agent, or Firm* — Allen, Dyer, Doppelt + Gilchrist, PA

(57) ABSTRACT

A system for disinfecting an enclosed area may include at least one ultraviolet (UV) light and a fogging device which may include a portable housing, an atomizing disinfectant generator carried by the portable housing, and a processor carried by the portable housing. The processor may be configured to initiate a treatment cycle during which the atomizing disinfectant generator dispenses atomized disinfectant fluid into the enclosed area, after a first time period activate the at least one UV light while the atomized disinfectant fluid is being dispensed into the enclosed area, and after a second time period later than the first time period deactivate the at least one UV light and prior to completion of the treatment cycle.

17 Claims, 18 Drawing Sheets

Related U.S. Application Data which is a continuation of application No. 15/043,744, filed on Feb. 15, 2016, now Pat. No. 9,717,810.

(60) Provisional application No. 62/200,679, filed on Aug. 4, 2015, provisional application No. 62/115,871, filed on Feb. 13, 2015, provisional application No. 62/506,697, filed on May 16, 2017.

(51) Int. Cl.
| | |
|---|---|
| *B05B 1/08* | (2006.01) |
| *A61L 2/20* | (2006.01) |
| *A61L 2/24* | (2006.01) |
| *A61L 2/10* | (2006.01) |
| *A61L 2/18* | (2006.01) |
| *A61L 2/22* | (2006.01) |
| *A61L 9/14* | (2006.01) |
| *A61L 9/20* | (2006.01) |

(52) U.S. Cl.
CPC .................. *A61L 2/24* (2013.01); *A61L 9/14* (2013.01); *A61L 9/20* (2013.01); *A61L 2202/11* (2013.01); *A61L 2202/14* (2013.01); *A61L 2202/15* (2013.01); *A61L 2202/16* (2013.01); *A61L 2202/25* (2013.01); *A61L 2209/134* (2013.01)

(58) Field of Classification Search
USPC ........................... 422/5, 28, 306; 239/101
See application file for complete search history.

(56) References Cited

U.S. PATENT DOCUMENTS

| | | |
|---|---|---|
| 8,398,932 B2 | 3/2013 | Busujima |
| 9,717,810 B2 | 8/2017 | Grinstead |
| 2004/0005240 A1* | 1/2004 | Adiga ............... A61L 2/22 422/1 |
| 2011/0091354 A1* | 4/2011 | Schwartz ........... A61L 2/22 422/28 |
| 2013/0276357 A1 | 10/2013 | Shannon et al. |
| 2015/0020688 A1 | 1/2015 | Fairbank, Jr. et al. |
| 2017/0028407 A1 | 2/2017 | Fairbank, Jr. et al. |
| 2017/0333585 A1 | 11/2017 | Grinstead |

OTHER PUBLICATIONS

Canonical Robots: Health and Cleaning: UV and Spray Sterilization Robot; Retreived from internet Oct. 30, 2020; https://www.canonicalrobots.com/en/products/2040/14/health-and-cleaning/uv-and-spray; pp. 5.

* cited by examiner

FOGGING SYSTEM PROVIDING ATOMIZED SOLUTION AND ULTRAVIOLET LIGHT TO TREATMENT AREA

CROSS-REFERENCE TO RELATED APPLICATIONS

This application is a continuation-in-part of U.S. application Ser. No. 15/658,803 filed Jul. 25, 2017; which is a continuation of U.S. application Ser. No. 15/043,744 filed Feb. 15, 2016, which claims the benefit of provisional app. No. 62/115,871 filed Feb. 13, 2015, provisional app. No. 62/200,679 filed Aug. 4, 2015 and provisional app. No. 62/506,697 filed May 16, 2017, which are hereby incorporated herein in their entireties by reference.

TECHNICAL FIELD

The present invention relates to the field of disinfecting, deodorizing, preserving, or sterilizing, and, more particularly, to apparatuses and methods for delivery of disinfecting, deodorizing, preserving, or sterilizing solutions.

BACKGROUND

Disinfection and sterilization are particularly important in the field of healthcare to ensure that infectious pathogens are not transmitted to patients via medical devices or the environment in which patients are treated. While medical instruments may be placed in autoclaves or other sterilization chambers for sterilization, sterilization of the atmosphere and surfaces within a patient or operating room can be more difficult and labor intensive to perform properly. Moreover, there is evidence to show that a manual "spray and wipe", in addition to being labor and time intensive, is not always a suitably effective process for disinfection. More particularly, spray and wipe allows for human error (missing areas where pathogens reside), and may also allow for cross-contamination (spreading of germs).

While spray and wipe processes remain an important component of a disinfection strategy for certain applications, more contemporary methods such as fogging for whole room disinfection may be desirable to help ensure that all surfaces, whether visible or not, are reached for effective pathogen elimination.

SUMMARY

A system for disinfecting an enclosed area may include at least one ultraviolet (UV) light and a fogging device which may include a portable housing, an atomizing disinfectant generator carried by the portable housing, and a processor carried by the portable housing. The processor may be configured to initiate a treatment cycle during which the atomizing disinfectant generator dispenses atomized disinfectant fluid into the enclosed area, after a first time period activate the at least one UV light while the atomized disinfectant fluid is being dispensed into the enclosed area, and after a second time period later than the first time period deactivate the at least one UV light and prior to completion of the treatment cycle.

More particularly, in one example embodiment the at least one UV light may be carried by the portable housing. For example, the portable housing may have a plurality of sides and a top, and the at least one UV light may be a plurality of UV strip lights carried by the sides and top of the portable housing. In accordance with another example implementation, the fogging device may further include an output carried by the portable housing and coupled to the processor, and the processor may activate the at least one UV light via the output. By way of example, the output may comprise a wireless communications port.

The disinfectant fluid may comprise hydrogen peroxide, for example. Furthermore, the treatment cycle may include a saturation phase wherein the atomizing disinfectant generator operates to dispense atomized disinfectant fluid continuously to bring the enclosed area to a target saturation level, and a pulse phase wherein the atomizing disinfectant generator operates to intermittently dispense atomized disinfectant fluid to maintain the enclosed area at the target saturation level; and wherein the first time period occurs during the saturation phase.

In one example implementation, the atomizing disinfectant generator may include a disinfectant fluid reservoir for holding the disinfectant fluid, a compressor coupled to the disinfectant fluid reservoir, and an atomizing nozzle in fluid communication with the disinfectant fluid reservoir. The fogging device may further include a first wireless transceiver carried by the portable housing and coupled to the processor, and the system may also include a wireless communications device including a second wireless transceiver configured to remotely communicate with the processor of the fogging device and cause the processor to initiate the treatment cycle.

A related fogging device, such as the one described briefly above, and associated method for disinfecting an enclosed area using a fogging device and at least one UV light are also provided. The method may include initiating a treatment cycle during which the atomizing disinfectant generator dispenses atomized disinfectant fluid into the enclosed area. After a first time period, the at least one UV light is activated from the fogging device while the atomized disinfectant fluid is being dispensed into the enclosed area. After a second time period later than the first time period, the at least one UV light is deactivated from the fogging device and prior to completion of the treatment cycle.

DETAILED DESCRIPTION

Figure 1:
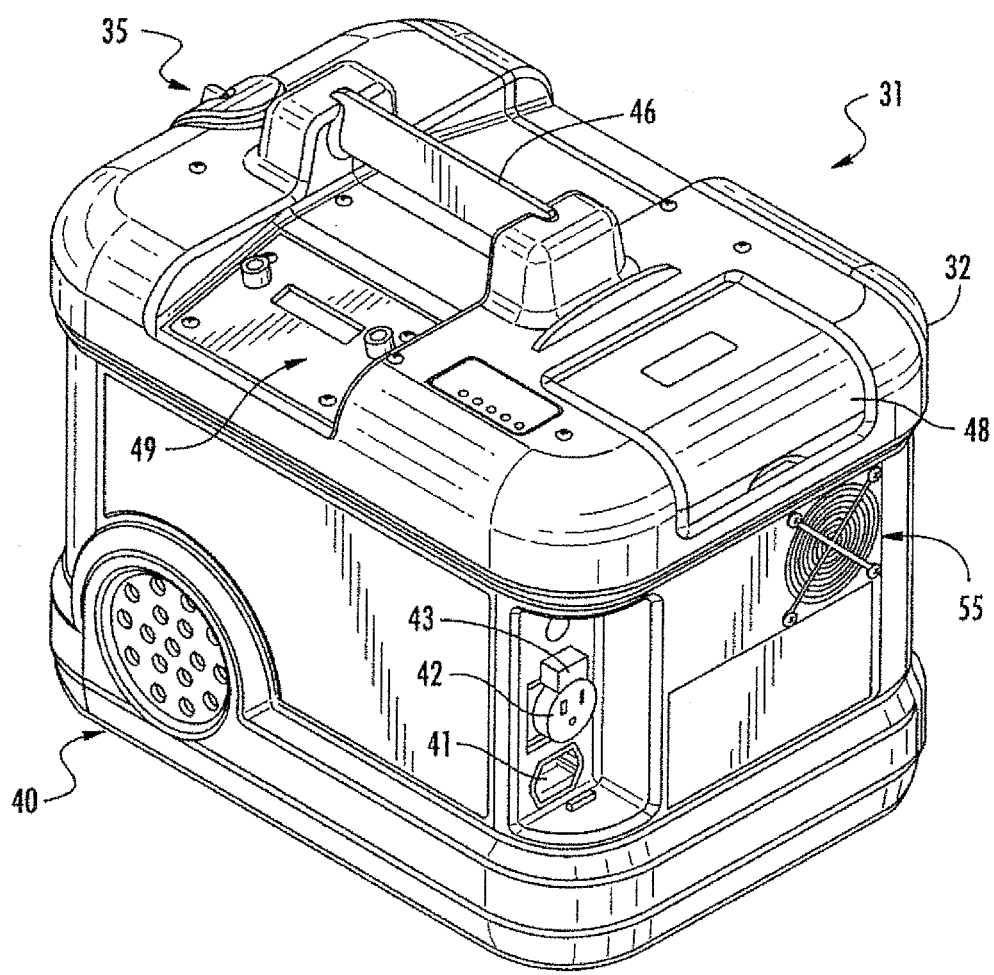
FIG. 1 is perspective view of a fogging device in accordance with an example embodiment.
Figure 2A:
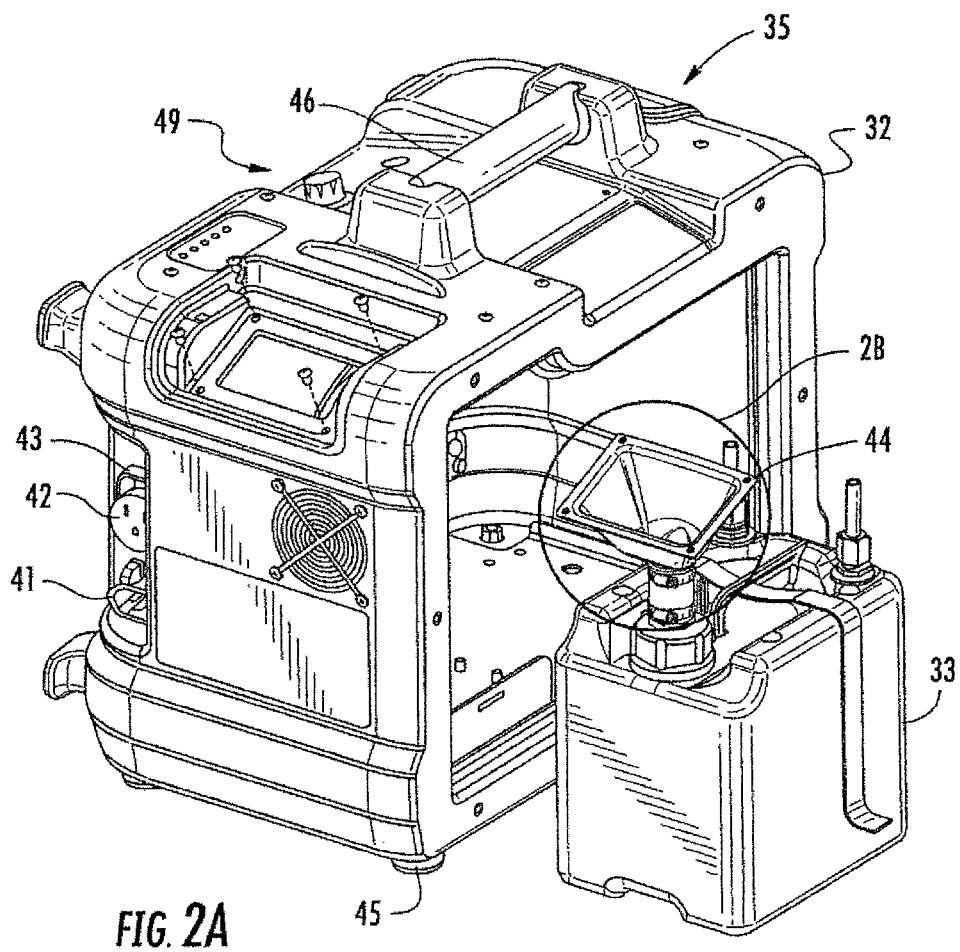
FIG. 2A is a perspective view of the fogging device of FIG. 1 with a side panel removed and illustrating installation of a fluid reservoir therein.
Figure 2B:
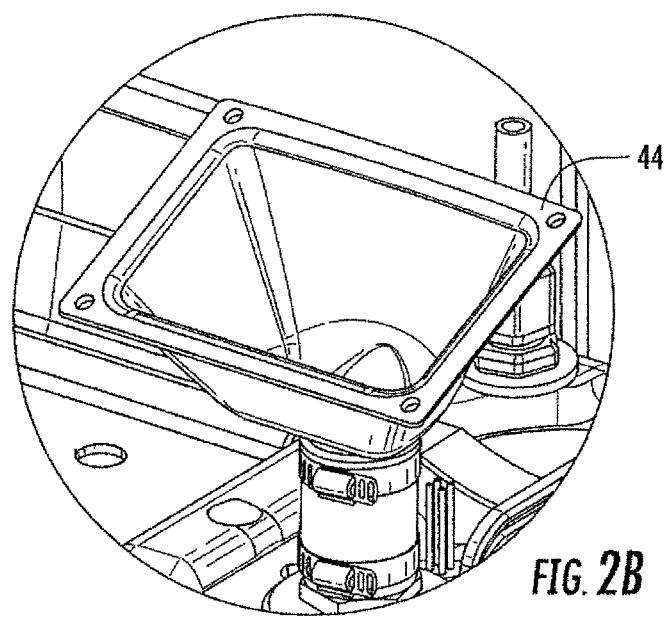
FIG. 2B is a perspective view of the area B of FIG. 2A illustrating an example funnel assembly for the fluid reservoir in greater detail.
Figure 3:
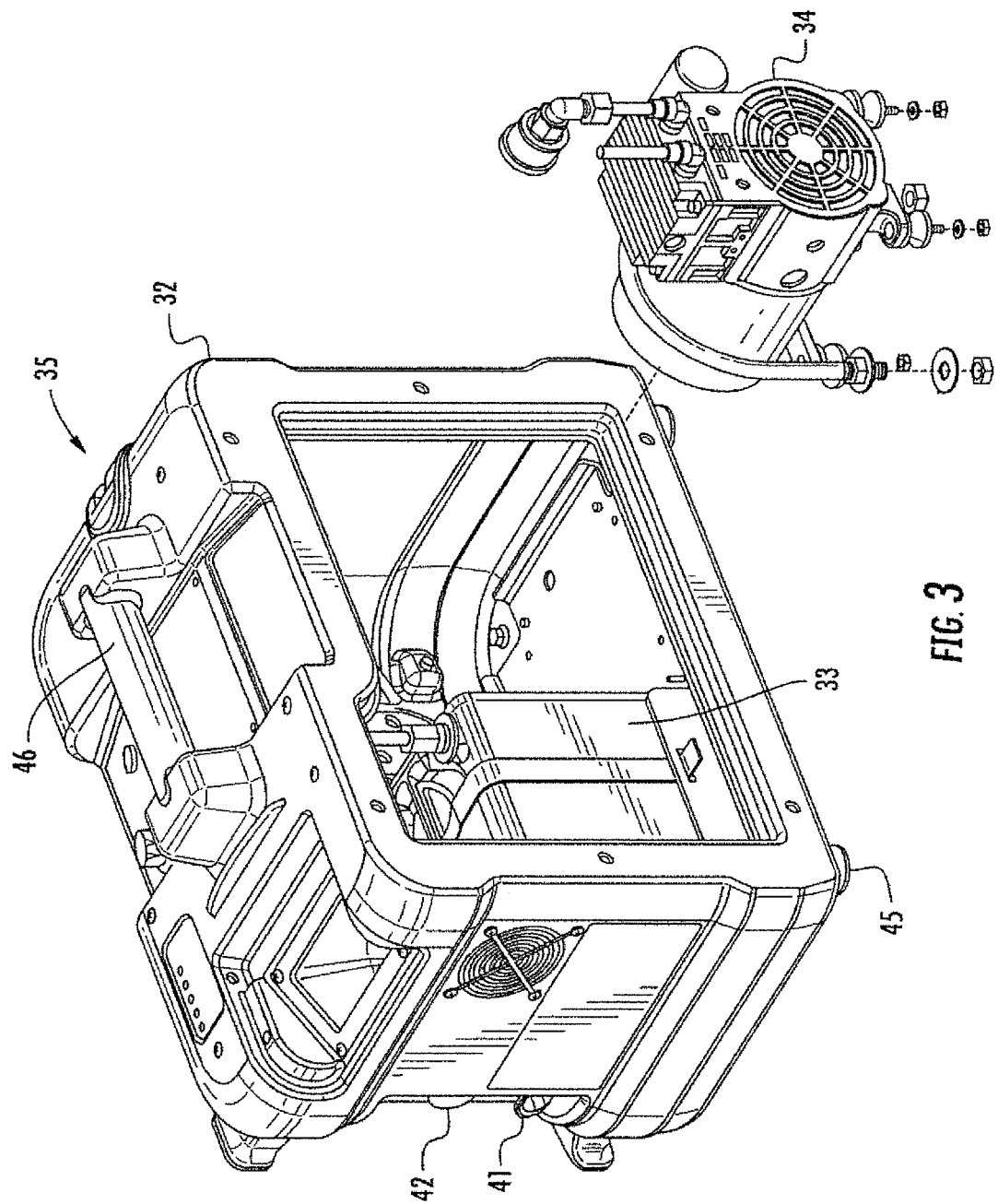
FIG. 3 is a perspective view of the fogging device of FIG. 1 with the side panel removed and illustrating installation of a compressor therein.
Figure 4:
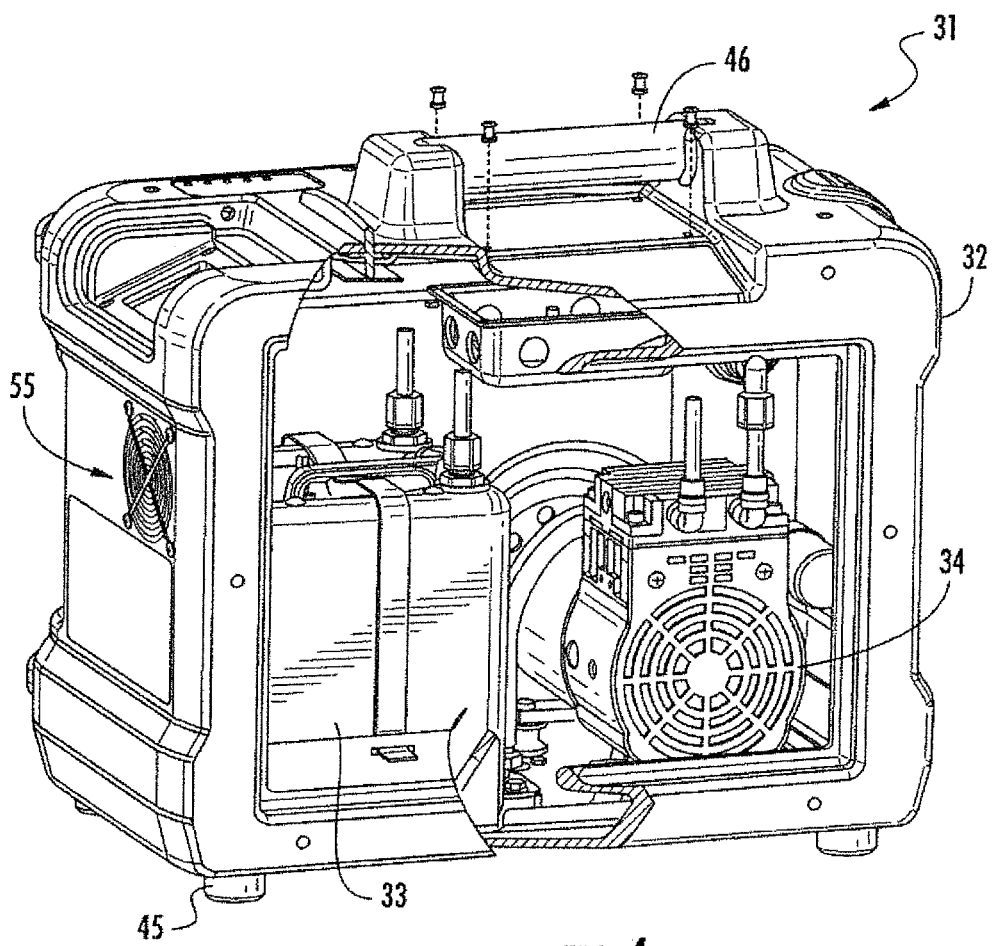
FIG. 4 is a perspective view of the fogging device of FIG. 1 with the side panel removed after installation of the fluid reservoir and compressor.

The present disclosure is provided with reference to the accompanying drawings, in which various embodiments are shown. However, other embodiments in many different forms may be used, and the disclosure should not be construed as limited to the particular embodiments set forth herein. Rather, these embodiments are provided so that this disclosure will be thorough and complete, and will fully convey the claim scope to those skilled in the art. Like numbers refer to like elements throughout.

Referring initially to FIGS. 1-7 and 14, the present disclosure relates to a fogging or atomizing system 30 which may be used for the application of a chemical solution to a treatment area for the purposes of disinfecting, deodorizing, preserving, or sterilizing the area or items within the area, for example. By way of example, the fogging system may be used for application of a disinfectant chemical to an enclosed area, including one or more rooms in a building, as well as in vehicles such as busses, ships/boats, airplanes, subway or train cars, automobiles, trucks, etc. In the example illustrated in FIG. 7, those components schematically shown on the right of the vertical dashed line are considered to be within the enclosed treatment area.

The fogging system 30 illustratively includes a plurality of fogging devices or foggers 31 which are to be positioned within the enclosed treatment area (FIG. 7) to perform a treatment cycle. Each fogging device 31 illustratively includes a portable housing 32, and an atomizing fluid generator carried by the housing and including a fluid reservoir 33 carried by the housing, a compressor 34 carried by the housing and coupled to the fluid reservoir, and an atomizing nozzle 35 carried by the housing and in fluid communication with the fluid reservoir. The fogging device 31 further includes a first wireless transceiver 36 carried by the housing, and a first processor 37 carried by the housing and coupled to the compressor and the wireless transceiver.

The fogging device 31 may provide several advantages over conventional devices, in that it is relatively compact, rugged, and portable. In one example implementation, each fogging device 31 may provide an atomized solution of chemical to disinfect enclosed areas up to 10,000 square feet for a one gallon fluid reservoir, although the size of the fogging device 31 and reservoir may be changed for treatment of areas of different sizes. By way of example, the fogging device 31 may be used in medical, mold remediation, commercial and residential applications, as well as other areas. Furthermore, in addition to disinfecting, deodorizing, preserving, or sterilizing applications, the fogging device 31 described herein may also be used for other applications such as the delivery of pesticides (e.g., for termite, mosquito, bedbug, or general pest prevention chemicals). In some embodiments, the fogging device 31 may also be used in a semi-enclosed or open area, in addition to treating enclosed areas.

The housing or case 32 of the fogging device 31 may be a relatively compact and rugged rotomold construction, and in the illustrated example it includes molded banding along the bottom and top of the unit encompassing one or more round air intakes 40 (although air intake or exhaust ports may be located at different locations on the housing). The fogging device 31 also illustratively includes cut-outs for power entry 41, an output(s) 42 (e.g., an electrical AC outlet), and associated circuit breaker 43. A fill cover 48 (FIG. 1) is over an integrated funnel 44 (FIG. 2B), which leads to the chemical solution reservoir 33 (e.g., a one-gallon reservoir, although other sizes may also be used). By way of example, feet 45 (e.g., rubber) may be coupled to the bottom of the housing 32 (four are shown in the example embodiment, although other numbers may be used in different embodiments). Cord wraps (made of injection mold) may be used to stow the power cord in some embodiments, if desired.

The form factor of the fogging device 31 allows for relatively easy transportation, as well as stability during transport. An integrated handle 46 also allows for ease of carrying. In the example embodiment, the total size of the unit is 19¾" long×14½" wide by 17¼" high, although different dimensions and case shapes may be used in different embodiments. Metal reinforcing mounting plates may also be used inside the housing 32 to mounting the various internal components and increase ruggedness and structural integrity.

Figure 5:
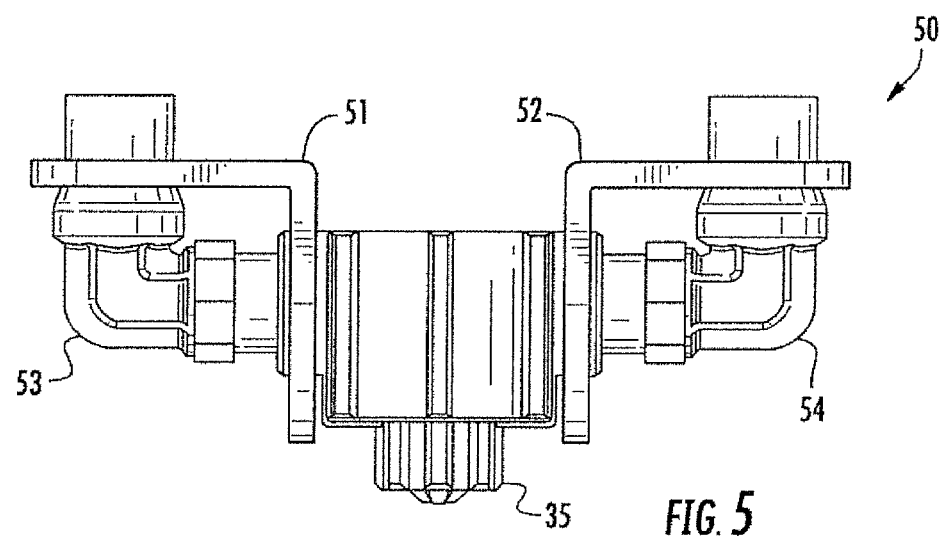
FIGS. 5 and 6 are top and side views, respectively, of an example nozzle assembly for the fogging device of FIG. 1.
Figure 6:
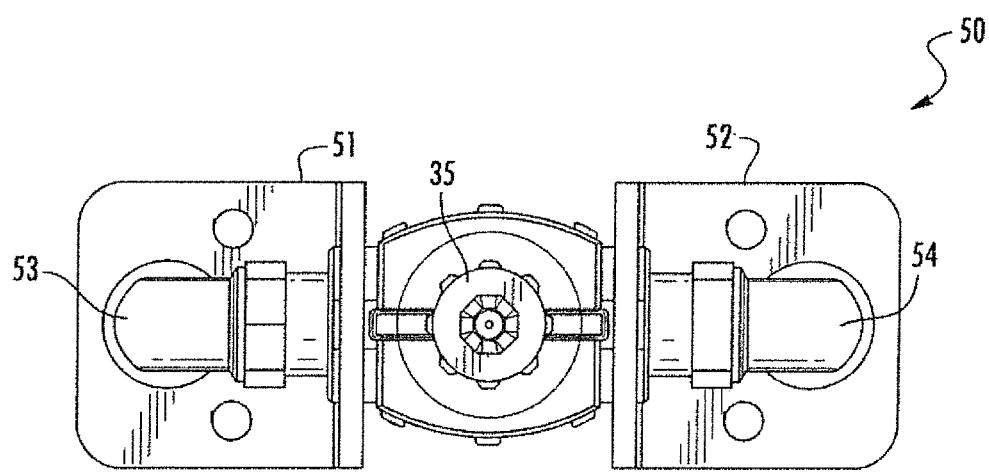
Figure 7:
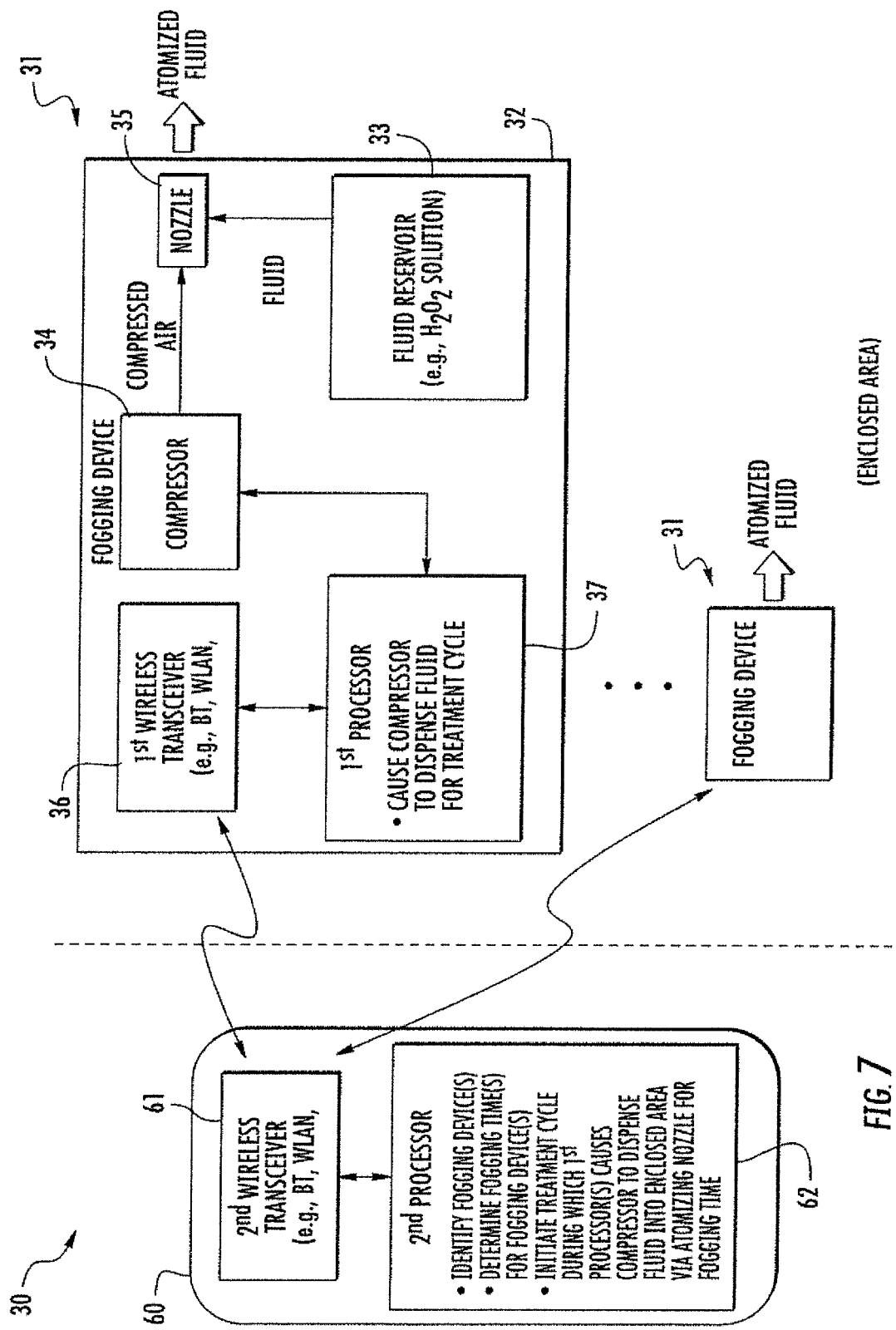
FIG. 7 is a schematic block diagram illustrating a system for treating an enclosed area with an atomized fluid which may include a plurality of the fogging devices of FIG. 1.

The atomizing nozzle 35 is carried by a nozzle holder assembly 50, which allows the nozzle to be adjustable to multiple dispensing positions ranging from vertical to horizontal (although a greater range of adjustability than 90° may be used, if desired). That is, the nozzle holder assembly 50 advantageously allows fogging vertically or horizontally as conditions require. More particularly, the nozzle holder assembly illustratively includes two "L" shaped or 90° brackets 51, 52 with a hole through each side or leg of the bracket. The holes in the bracket 51 allow a feed pipe 53 to supply compressed air from the compressor 34 to the atomizing nozzle 35, while the holes in the bracket 52 allow a feed pipe 54 to supply chemical fluid from the fluid reservoir 33 to the atomizing nozzle 35 (FIGS. 5 and 6). In some embodiments, an optional filter may also be connected in-line between the fluid reservoir 33 and the atomizing nozzle 35. The nozzle 35 is pivotally coupled to the brackets

51, 52 to allow the above-noted rotation from horizontal to vertical orientations (or otherwise), as desired. The fluid reservoir 33 may optionally include a vent, such as with barb fitting, for example. In some embodiments a strap may be used to add further stability to the fluid reservoir 33 within the housing 32, although this is not required in all configurations.

In some embodiments, an actuator may be included that is controlled by the first processor 37 to move the nozzle 35 during the treatment cycle for enhanced fog circulation, if desired. Also, in other embodiments, more than one atomizing nozzle 35 may be used, as well as different mounting configurations, along with an appropriately sized compressor to provide increased atomized spray output. One example atomizing nozzle 35 which may be used is part no. 1/4J-SU2A from Spraying Systems Co. of Wheaton, Ill., for example, although other suitable atomizing nozzles may be used in different embodiments. Moreover, different atomizing nozzles may be interchanged for different chemicals, and in some embodiments the processor 37 may accommodate different treatment schedules and/or parameters (e.g., times, pressures, etc.) for different nozzles and treatment chemicals, to allow use of the same fogging device 31 for a variety of different treatment applications. Such treatment schedules and/or parameters may be implemented at the time of manufacture of the fogging device 31, as well as by firmware updates at a later time, as will be discussed further below.

The fogging device 31 may be assembled with the fluid reservoir 33 and compressor 34 being riveted to the interior of the case or housing 32 (although other suitable connectors, such as screws, bolts, etc., may also be used). Recessed rotomolded groves may also be provided in the case for side panel attachment, if desired.

In the illustrated example embodiment, the outlet 42 is a 120V outlet to plug in an air scrubber/filter or dehumidifier to aid in shortening the time required to clear the disinfected area after application of the chemical disinfectant solution, as will be discussed further below. The outlet on/off power may be sequenced by the processing circuitry, i.e., the first processor 37, carried on the included circuit board(s) (not shown), for example. The processing circuitry may be implemented using a combination of hardware (e.g., microprocessors, etc.) and a non-transitory computer-readable medium having computer-executable instructions for causing the processing circuitry to perform the various control operations for the fogging system. One or more case fans 55 may also be provided to aid in housing and compressor cooling, which may also be controlled by the processing circuitry.

Figure 8:
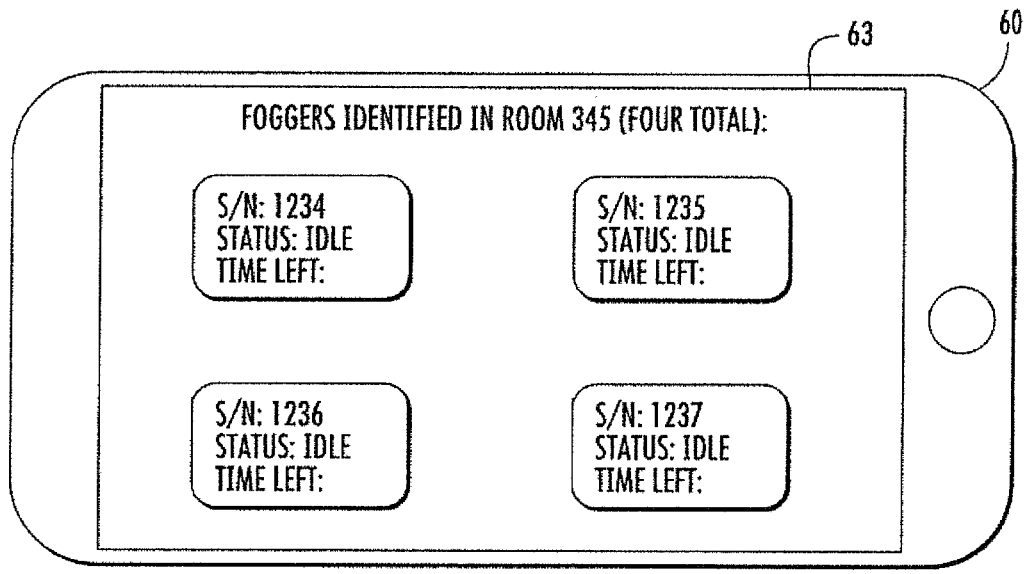
FIGS. 8-11 are screen shots of a mobile wireless communications device which may be used with the system of FIG. 7 illustrating various control screens for operating the fogging devices.

By way of example, the first wireless transceiver 36 (which may also be carried on an internal circuit board) may be a Bluetooth, Wi-Fi (WLAN), WiMax, cellular, or other suitable wireless transceiver which may be used to wirelessly interface the first processor 37 with other fogging devices 31, wireless humidity sensors, wireless filters or dehumidifiers, as well as one or more mobile wireless communications devices 60 (e.g., smart phones, tablet computers, laptops, etc.). In the illustrated example, the wireless communications device 60 is a smart phone including a second wireless transceiver 61 and a second processor 62. With reference to the flow diagram 140 of FIG. 14, beginning at Block 141, the second processor 62 may be programmed to identify the plurality of fogging devices 31 within the enclosed area based upon the first and second wireless transceivers, at Block 142. In accordance with one example implementation shown in FIG. 8, the second processor identifies that there are four fogging devices 31 within wireless communication range which have serial nos. 1234, 1235, 1236, and 1237 as indicated on a display 63 of the mobile wireless communications device 62.

In addition to an identifier (e.g., serial no.) of the identified fogging devices 31, various other types of information or events for each fogging device may also be provided to the wireless communications device 60, including a status of each fogging device 31, a time left in the fogging cycle, etc. For example, treatment cycle status information may be provided, such as when the treatment cycle has been initiated, how much treatment time left, and when the treatment cycle is complete. Another event is when the treatment area is safe to enter. For example, the treatment area may be safe to enter after a delay period following treatment. In another example, the treatment area may be safe to enter after an associated air filtering or dehumidification process is complete following treatment, as will be discussed further below. An audible alarm may also be provided to indicate one or more of the following events. Moreover, other information which may be communicated to/from the fogging system may include start/stop commands, a pause or delay command, updated status requests, tank fill level, operating temperature, etc., for example.

Figure 9:
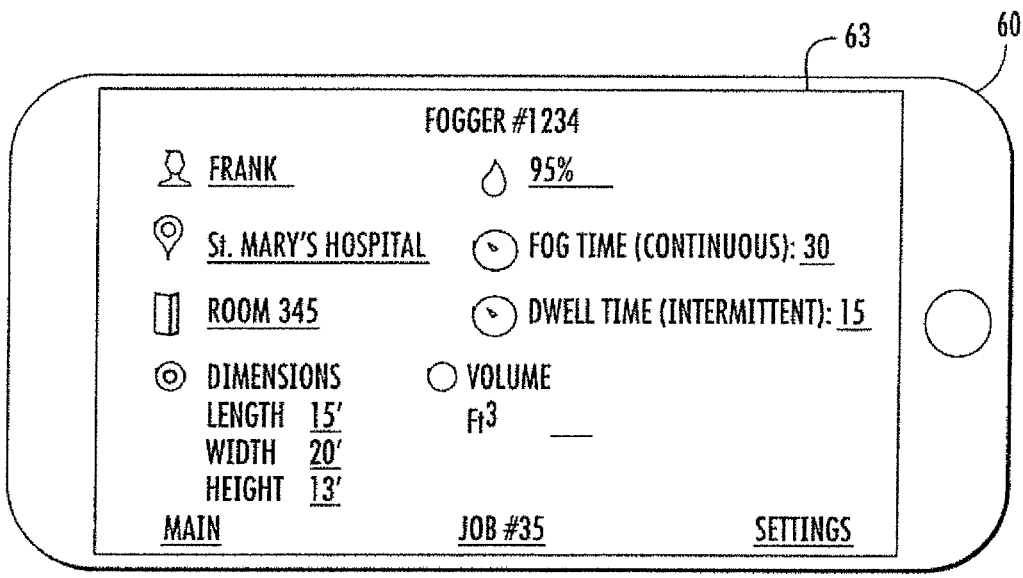

In another example shown in FIG. 9, the mobile wireless communications device 60 may allow a user to input certain parameters associated with the treatment job to be performed. In this example, an operator's name (here "Frank") may be provided, along with a name of the building or job site ("St. Mary's Hospital"), a room number of the job ("345"), the dimensions and/or volume of the room to be treated, a target humidity level (here 95%), as well as fog time (here 30 minutes) and pulse time (here 15 minutes). Moreover, these settings may also be saved in memory as a job and assigned a respective number (here job #35) so that the next time a treatment is performed the job particulars need not be input again.

For the present example where multiple fogging devices 31 are present in the enclosed treatment area, the second processor 62 may determine respective fogging times for the plurality of fogging devices based upon a size of the enclosed area and the number of fogging devices identified within the enclosed area, at Block 143. More particularly, multiple fogging devices 31 may advantageously be used in conjunction for the treatment of larger areas, or to expedite the treatment of a smaller more critical area that needs to be turned around quickly (e.g., an operating room, etc.). Knowing the fluid dispensing rate of the fogging device 31 for a given chemical, the desired saturation level, and the size (e.g., entered volume or volume calculated based upon the entered room dimensions), the second processor 62 may calculate the respective times that the fogging device will need to run continuously to reach the desired saturation level. Generally speaking, the desired saturation level may be selected so that the concentration of the chemical is at a maximum level before condensation begins on surfaces in the enclosed area.

In the present example, each fogging device 31 will only need to run 1/4 of the time it otherwise would if it was the only fogging device in the enclosed area (since there are four fogging devices). Generally speaking, each fogging device 31 will be assigned an equal treatment or fogging time, but in some embodiments different devices may be assigned different fogging times. This could be based upon different fluid levels in each of the fogging devices 31, different flow rates of the identified fogging devices, operational hours on each fogging device, etc.

Moreover, respective pulse times may also be assigned to each fogging device 31. During a pulse cycle, the fogging device may cycle on and off to help keep the enclosed area at the desired humidity level without oversaturating the enclosed area. Moreover, this may also help to conserve treatment fluid. When multiple fogging devices 31 are being used, their pulse times may be coordinated to be on (i.e., dispensing fluid) at the same time, or to turn on at different (staggered) times, if desired.

Once the fogging times are determined for the fogging devices 31, the second processor 62 may initiate a treatment cycle during which, on a coordinated schedule, the first processor 37 of each fogging device 31 causes its associated compressor 34 to dispense fluid from the fluid reservoir 33 into the enclosed area via the atomizing nozzle 35 for the respective fogging time of the fogging device, at Block 144. The fogging devices 31 may then run for the designated fogging times in a continuous mode so that the enclosed area reaches the desired saturation level, at Block 145, after which the optional pulse phase may occur for the appropriate amount of time, at Block 146, which illustratively concludes the method of FIG. 14 (Block 147). In the example implementation shown in FIG. 9, a $H_2O_2$ fogging solution (i.e., a mixture of $H_2O_2$ and water) is used for a disinfection treatment in a hospital room, with a desired saturation level of greater than 85%, and more particularly between 90 and 95%, although other types of treatment chemicals and appropriate saturation levels may be used for different applications in different embodiments. An example pulse phase for this use case may be 45 seconds on, 15 seconds off during each minute of the pulse phase, although other cycle times may be used in different embodiments.

Generally speaking, Applicant theorizes without wishing to be bound thereto that during the fog or saturation phase, enough chemical should be added to the enclosed area to bring the area to around 90% relative humidity or more for the above-described $H_2O_2/H_2O$ mixture. More particularly, with such a chemical mixture, when the relative humidity is above 85% then the enclosed area may be considered to be in the "kill zone" where most if not all pathogens will be killed if exposed for a sufficient duration at this concentration. Thus, the amount of time necessary for the fog or saturation cycle may vary depending on the starting relative humidity, and additional time may be required where the starting humidity is relatively low, for example, to reach the kill zone. The purpose of the pulse phase is to keep the enclosed area in the kill zone.

In accordance with another example dwell cycle implementation, the pulse phase may be broken into five minute programmable segments (although other durations may also be used). Each segment may include compressor cycling on/off for a given time (e.g., 100 seconds off, 100 seconds on, 100 seconds off, although other durations may be used and the on/off times may be different). This ratio may change based upon the given fog or saturation time. That is, for a shorter fog time there may be a shorter ON segment, and a longer fog time may have a longer ON segment, for example. The length of the pulse time may advantageously be adjusted (e.g., in a range of 10 to 40 minutes, although longer or shorter times may be used) based upon the particular pathogen(s) that is targeted. By way of example, a relatively short pulse phase of ten minutes may be sufficient for a relatively easy to kill pathogen, while a longer time (e.g., 25 minutes or more) may be used to kill *C. Difficile* (*C. diff*).

Figure 10:
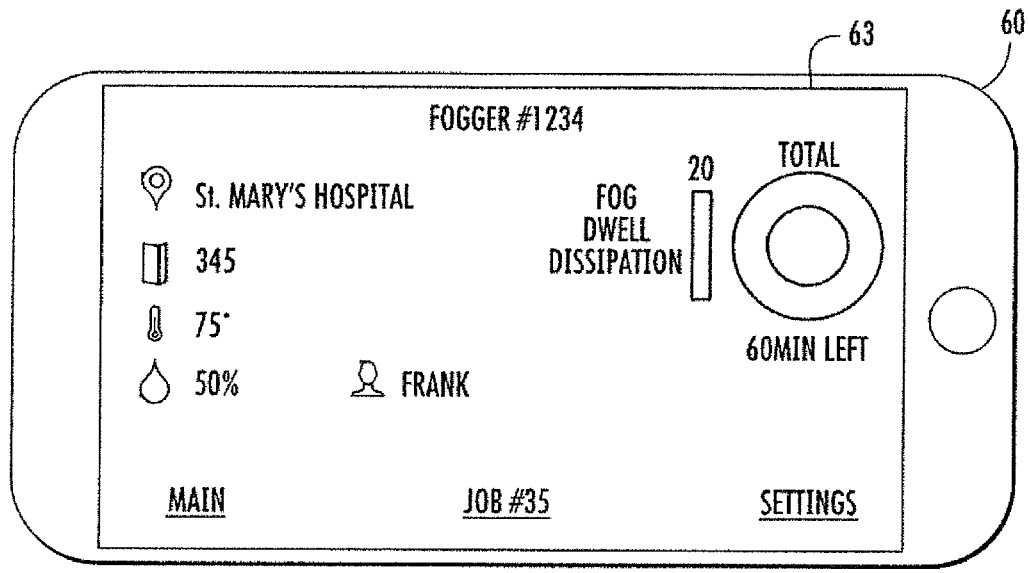

FIG. 10 shows an example screen shot during a treatment cycle indicating the status of the job being performed for the specific fogger with serial no. 1234. Here again, the building/room information and technician name are displayed, along with other parameters relating to the status of the job. More particularly, a temperature measured by an optional temperature sensor (not shown) of the fogging device 31 is displayed, a current measured humidity level is being displayed (which may be determined by a humidity sensor located in the room, as will be discussed further below, although there may be a humidity or micro-condensation sensor on the fogging device as well), as well as indicators of progress in the treatment cycle and time remaining. In should be noted that the screen shot of FIG. 10 may be based upon "real time" data when the first and second wireless transceivers 36, 61 are in range of one another, but the second processor 62 may also provide virtual or estimated information if the wireless transceivers are out of range. That is, the second processor 62 may keep its own estimated times to completion for each fogging device(s) 31, which is updated when in wireless communications range of the fogging device. Thus, if a technician leaves the vicinity of the enclosed area during the treatment cycle, he may still know the approximate status of each fogging device(s) 31 even though it is presently out of range.

In accordance with one example implementation, the plurality of fogging devices 31 may be wirelessly "daisy-chained" or otherwise connected together in a wireless network (e.g., an ad-hoc Wi-Fi network) to coordinate start/stop times for application to larger spaces. For example, an ad-hoc network may be established between a plurality of fogging devices 31 in one or more rooms of a building, etc., such that the wireless communications device 60 acts as a master device to coordinate start/stop times of the other devices between them (which act as slave devices). In this regard, the wireless communications device 60 may be a smart phone, tablet, etc., as noted above, or in other embodiments the wireless communications device may be may be a given fogging device 31 from which the treatment cycle is initiated for all of the remaining devices. In another example embodiment, the wireless communications device 60 (e.g., a smart phone, tablet computer, etc.) may pair with each of the fogging devices 31 individually (e.g., via Bluetooth), and cause them to start sequentially (i.e., one after the next), or to all begin fogging at the same time, for example. Thus, start/stop times for the different fogging devices 31 may be coordinated to occur at the same time, or to be staggered, as desired for a given implementation.

Figure 11:
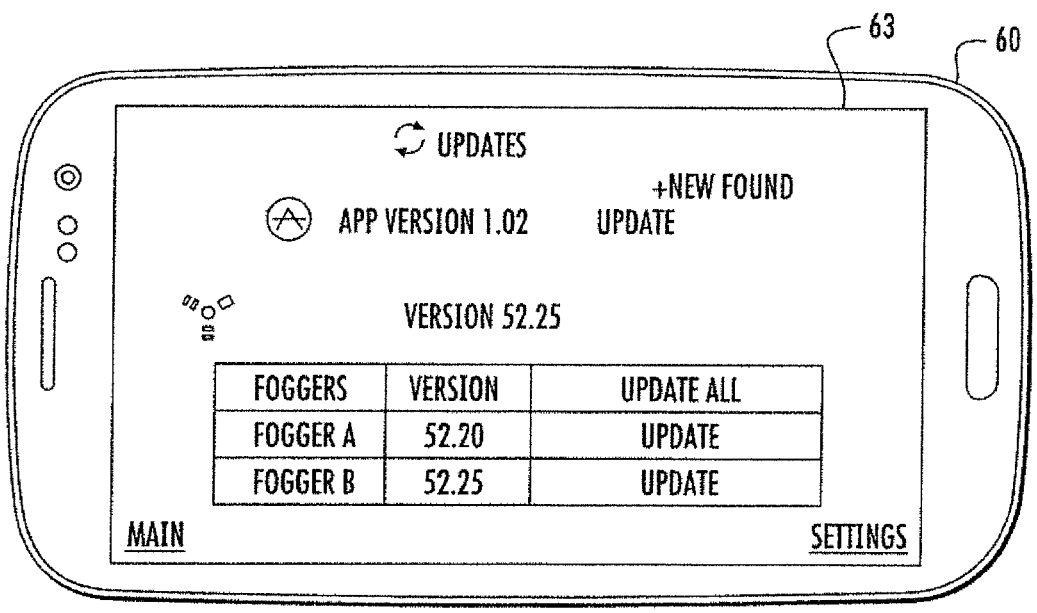

Referring additionally to FIG. 11, in some embodiments the wireless communications device 60 may be further programmed to provide firmware updates (e.g., retrieved via the Internet from the manufacturer) to the first processors 37 of each fogging device 31 via the first and second wireless transceivers 36, 61. In the illustrated example, two fogging devices 31 are identified (here labeled Fogger A and Fogger B), along with an indication of the firmware version that each is running (52.20 and 52.25, respectively). Moreover, a most current version of the firmware currently available (here version 52.25) is also provided, along with a selection button or link to download or push the update to the given fogging device 31. Moreover, this illustrated screen also provides an indication of the version of the app running on the mobile wireless communications device 60 (here version 1.02), along with a link or button that may be selected to update the app version.

The app may be provided by the manufacturer of the fogging devices 31 for users to install on different computing platforms (e.g., Android, iOS, etc.), and allow for future firmware upgrades to the fogging devices including, but not limited to, support for optional hardware (humidity sensors, $H_2O_2$ sensors, etc.), new treatment cycle profiles for different chemicals, etc. Similarly, the app may provide corresponding control options for such features on the display 63. The app may also display operational hours, maintenance issues, malfunctions, etc., which may occur with the fogging devices as well. Such information may be maintained by the first processor 37 of each fogging device 31 and locally stored, and it may be accessed via respective control panels 49 at each of the fogging devices as well. The control panel 49 may include a digital (e.g., LED) display and one or more input devices (e.g., buttons, knobs, etc.), for example. The app may also cause the first processor 37 to provide updates regarding usage and status of each fogging device 31 to a central location (e.g., manufacturer, service company, etc.) so that maintenance needs and job performance may be monitored, for example.

Figure 12:
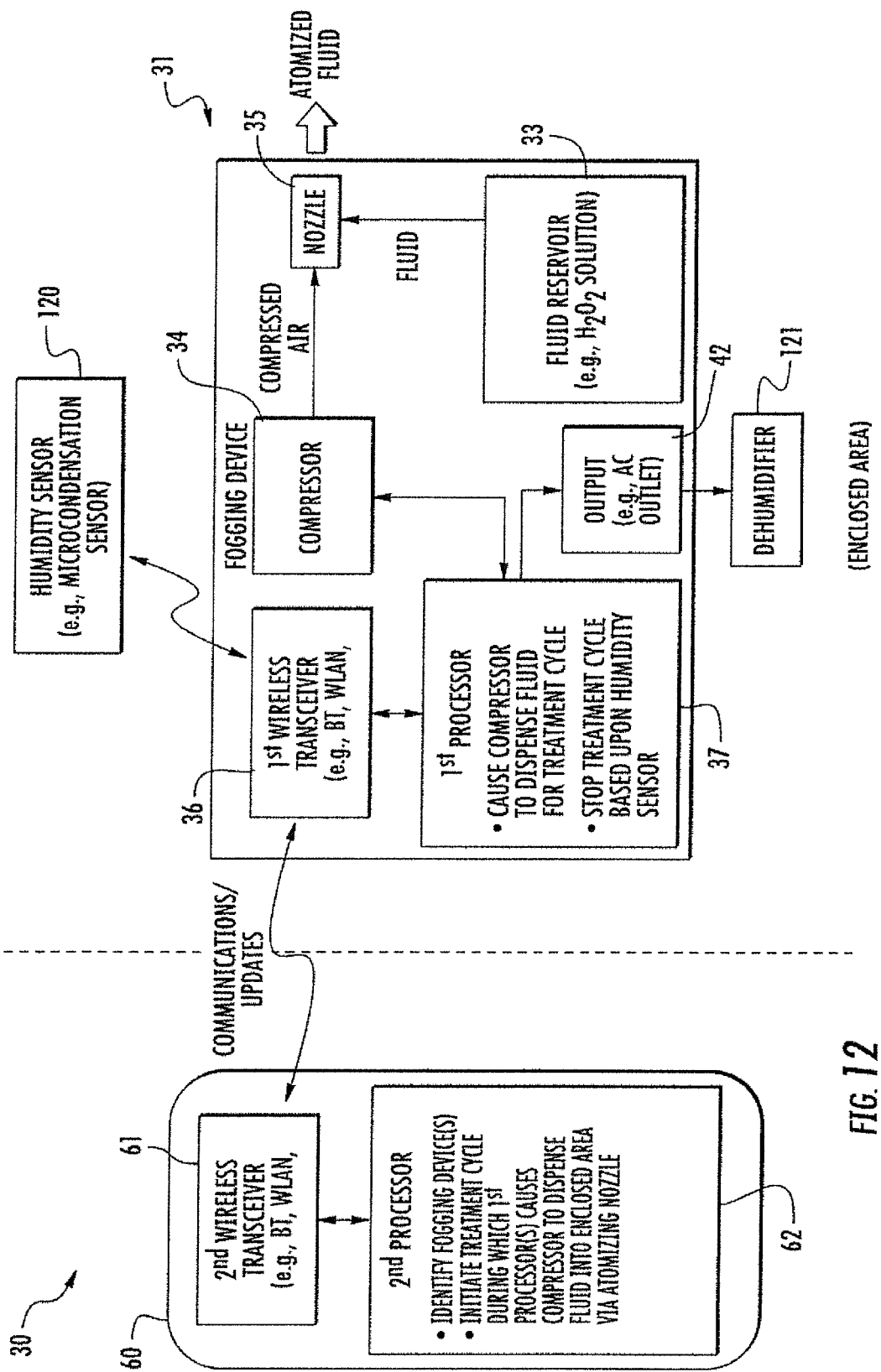
FIG. 12 is a schematic block diagram illustrating a system for treating an enclosed area in accordance with another example embodiment.
Figure 15:
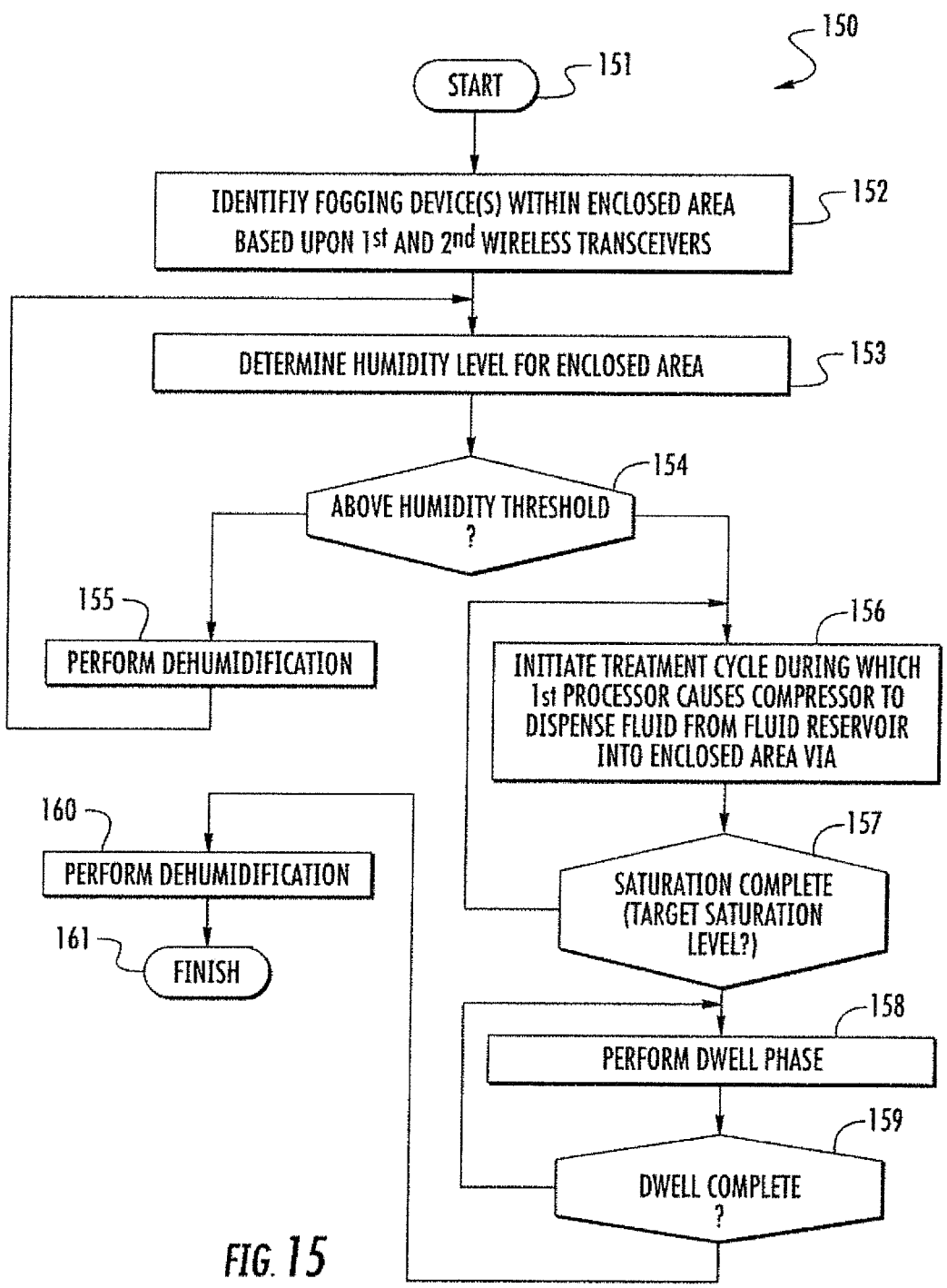
FIG. 15 is a flow diagram illustrating method aspects associated with the system of FIG. 12.

Turning now to FIGS. 12 and 15, in accordance with another example embodiment, a fogging device(s) 31 may be paired with a humidity sensor 120 for monitoring the humidity level in the enclosed area to control the fogging treatment cycle. In one example embodiment, the humidity sensor 120 may be a micro-condensation sensor, for example, although other types of humidity sensors may be used in different implementations (e.g., a $H_2O_2$ sensor, where are $H_2O_2$ treatment chemical is being used). In some applications, it may be desirable to place the humidity sensor 120 in the enclosed area apart from the fogging device 31, as illustratively shown in FIG. 12, to help ensure that the humidity reading more accurately reflects that of the overall area. However, in other applications the humidity sensor 120 may be incorporated or integrated in the fogging device 31 itself. In particular, if the nozzle 35 is directed out and away from the fogging device 31 (i.e., rather than straight up in the air), a built in humidity sensor 120 may provide desired readings as well. In such case, the humidity sensor 120 may be directly connected or hard wired to the first processor 37.

Beginning at Block 151 in the flow diagram 150, the fogging device 31 may be identified by the wireless communications device 60 as described above, at Block 152 (although in some embodiments the fogging device may be controlled locally and a separate wireless communications device need not be used to interface with the fogging device). The first processor 37 of the fogging device 31 may communicate with the humidity sensor 120 via the first wireless transceiver 36, although a wired link may also be used in some embodiments. The first processor 37 may thereby determine an initial humidity level for the enclosed area prior to the beginning of the treatment cycle, at Block 153.

Generally speaking, for some chemical solutions, greater efficacy may be achieved if the treatment is started when the humidity within the enclosed area is in a preferred or desired range. By way of example, with respect to a 95% $H_2O$ to 5% $H_2O_2$ disinfectant solution, Applicant theorizes without wishing to be bound thereto that greater efficacy is achieved if the treatment cycle is initiated when a relative humidity in the enclosed treatment area is between 30% and 50%.

To this end, a dehumidifier 121 may optionally be connected to the output 42 of the fogging device 31, and when the first processor 37 determines that the humidity level in the enclosed area is above 50% from the humidity sensor 120, the first processor may accordingly activate the output 42 to turn on the dehumidifier until the humidity level falls below the desired humidity threshold (here 50%, although other levels may be used in different applications), at Blocks 154-155. Conversely, in extremely dry climates, a humidifier may likewise be connected to the output 42 to perform humidification and raise the starting humidity for the enclosed area to the desired lower threshold for the effective starting humidity range (e.g., 30% in the above example). It should be noted that while the output 42 was described as an AC outlet above, in some embodiments this could be a low power output (e.g., USB port, etc.), or the humidifier, dehumidifier, filter, etc. may be controlled wirelessly, similar to the humidity sensor 120. In such cases, the dehumidifier (and/or humidifier) may be plugged into its own wall outlet, so that it need not receive power from the fogging device 31.

Once the humidity in the room is within the desired starting range (e.g., below 50% in the present example), the treatment cycle may be initiated (Block 156) during which the first processor 37 of the fogging device(s) 31 causes its associated compressor 34 to dispense fluid from the fluid reservoir 33 into the enclosed area via the atomizing nozzle 35, as discussed above. However, in this implementation, a fogging time for the fogging device(s) 31 need not be set or calculated by the second processor 62, as the first processor 37 may instead communicate with the humidity sensor 120 to determine when the humidity level in the enclosed area has reached the target saturation level from, fogging (e.g., 90% in the present example), at Block 157.

If a pulse phase is used for the particular treatment, as discussed above, intermittent cycling of the atomizing spray may be performed until the desired pulse time is completed, at Blocks 158-159. Stated alternatively, it is the determination by the humidity sensor 120 that the target saturation level has been reached that triggers stopping of the saturation or fog phase of the treatment cycle, and the beginning of the pulse phase of the cycle (if used in the given embodiment). Again, the pulse time may be based upon the particular chemical being used, and how long the enclosed area needs to remain at the saturation level for the given application. In the above example, the pulse phase may be used to help keep the relative humidity in approximately the 80-95% range (although different target saturation levels and pulse ranges may be used for different types of chemicals). Controlling the treatment cycle based upon measured humidity, rather than a timed cycle, may be helpful in area where there is a significant amount of drapes, carpet, bedding, etc., which tend to absorb some of the atomized fluid such that a longer saturation phase may be required to get the enclosed area up to the target saturation level as compared to a "bare" room.

In embodiments where the dehumidifier 121 is optionally used, upon completion of the pulse phase the first processor 37 may activate the dehumidifier (Block 160) to help dissipate the chemical in the enclosed area and bring the humidity level back down to a normal level. This may advantageously help make the room safe to enter more quickly than simply waiting for the room to air out. The method of FIG. 15 illustratively concludes at Block 161.

Figure 13:
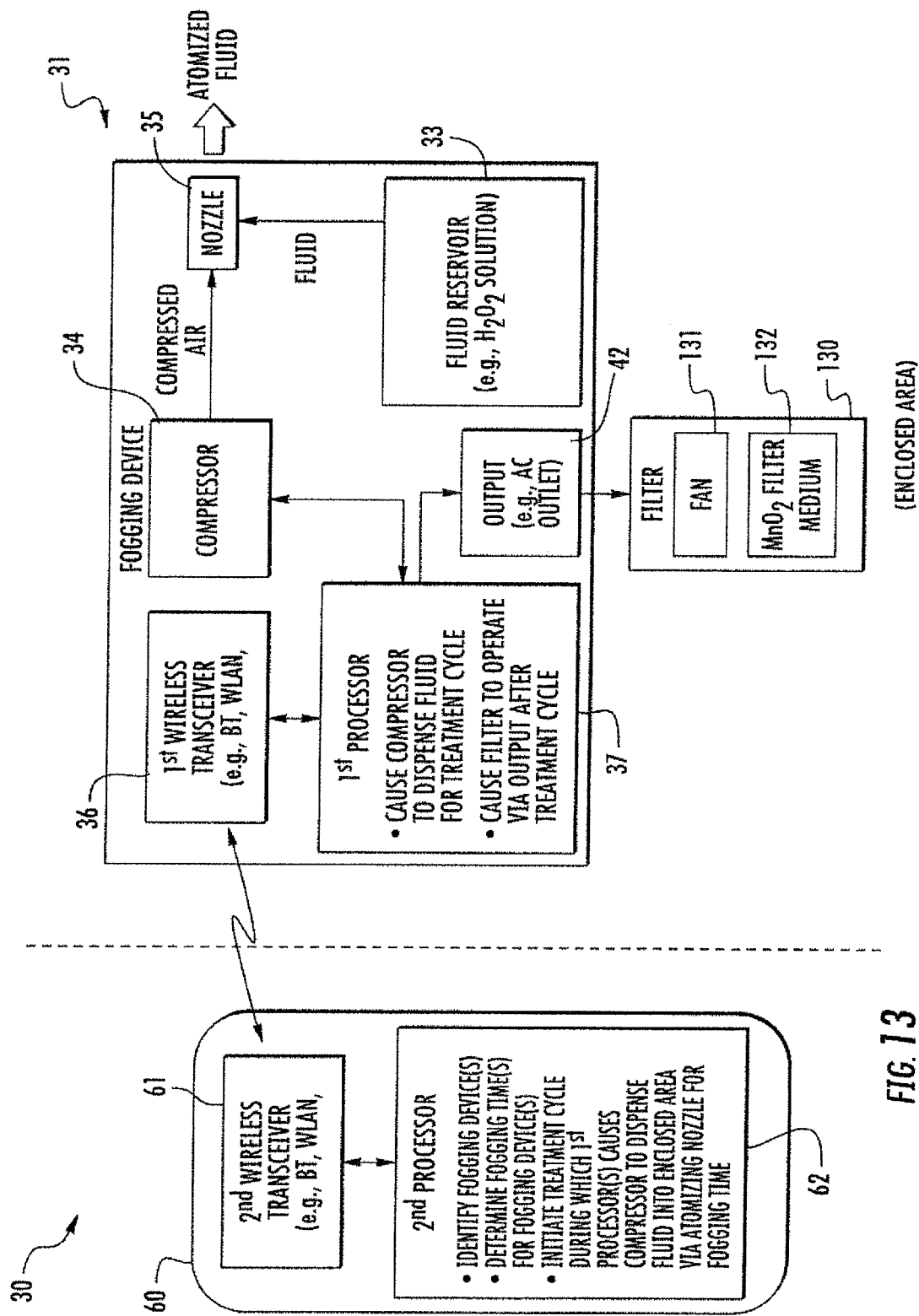
FIG. 13 is a schematic block diagram illustrating a system for treating an enclosed area in accordance with still another example embodiment.
Figure 14:
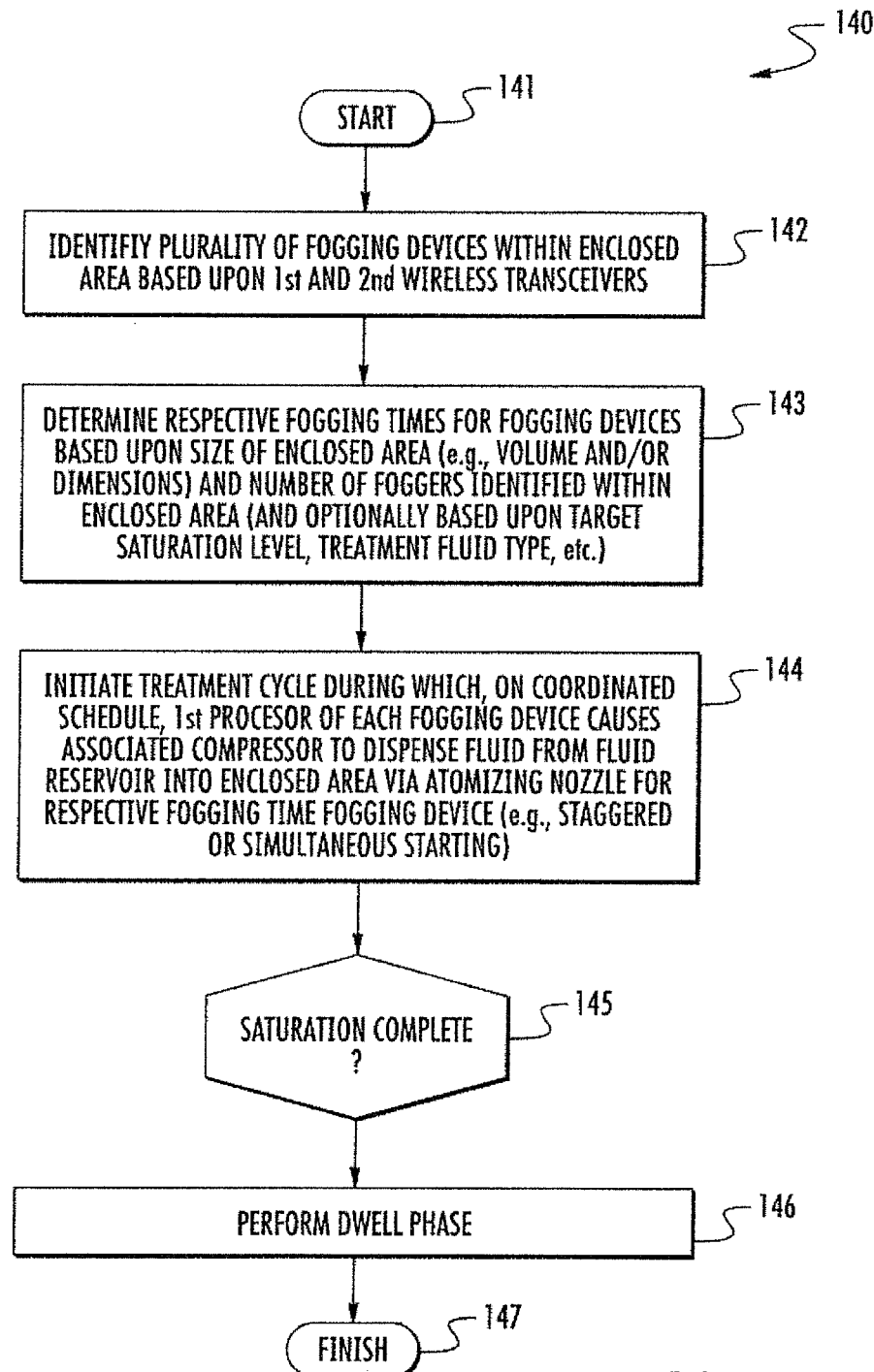
FIG. 14 is a flow diagram illustrating method aspects associated with the system of FIG. 7.
Figure 16:
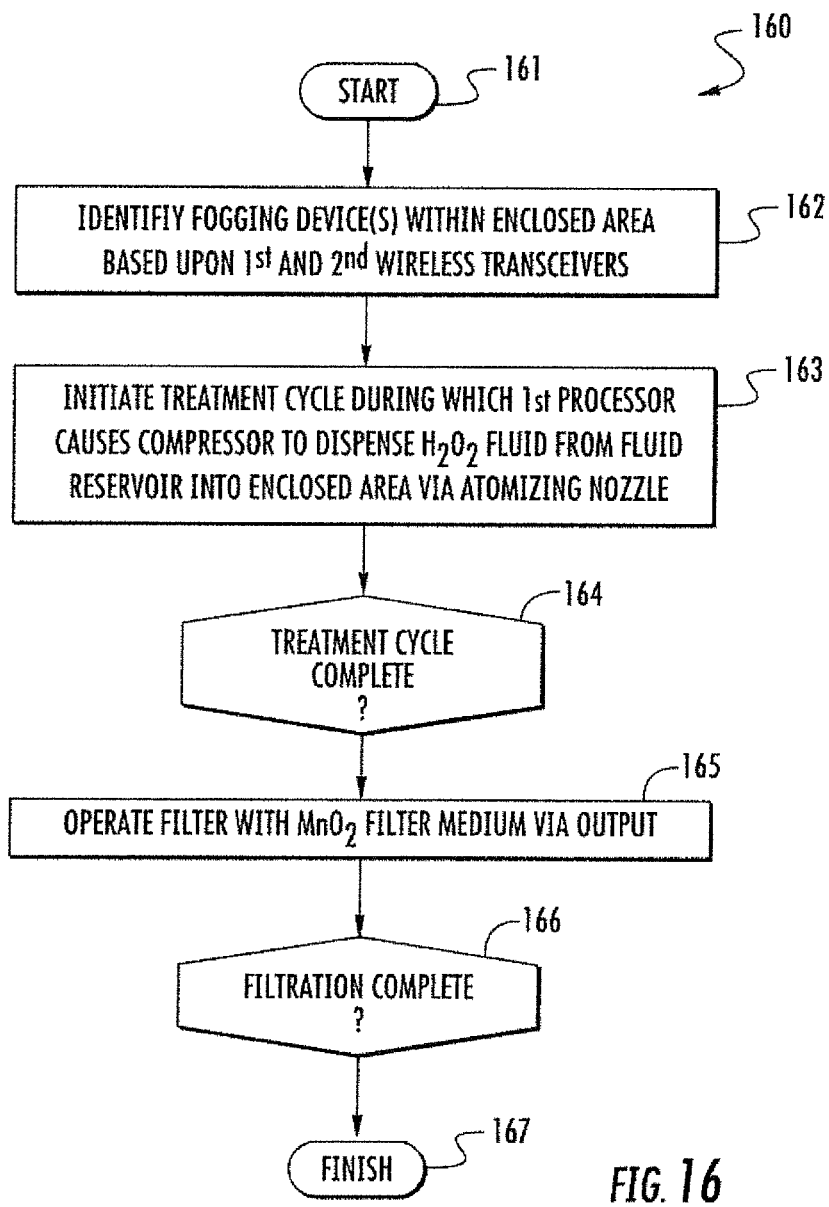
FIG. 16 is a flow diagram illustrating method aspects associated with the system of FIG. 12.

Turning additionally to FIG. 13 and the flow diagram 160 of FIG. 16, another example embodiment is now described in which an optional filter 130 is coupled to the output 42 of the fogging device 31. Beginning at Block 161, The fogging device(s) 31 in the enclosed area may be identified, and the treatment cycle initiated, by the wireless communications device 60 as described above (Blocks 162-163), although it should be noted that a fogging cycle may be initiated directly at the fogging device via the control panel 49 as well without using the wireless communications device in some embodiments. Once the treatment cycle is completed (which may include a saturation phase only, or saturation and pulse phases (as discussed above), at Block 164, the first processor 37 may then operate the filter 130 via the output 42, similar to the way in which the dehumidifier 121 is operated, as described above. The method concludes after the filtration is complete, at Blocks 166-167.

The filter 130 illustratively includes a fan 131 to circulate air through or over a filter medium 132. While various types of filters may be used and coupled to the output 42 of the fogging device 31, for example, for the above-described example of a hydrogen peroxide ($H_2O_2$) based treatment solution, a manganese dioxide ($MnO_2$) filter medium may be particularly helpful to dissipate or neutralize the $H_2O_2$ in the room. Here again, this will more rapidly bring the concentration of the chemical in the room to a level that is safe, allowing the room to be turned around more quickly for its next use. This may be particularly advantageous in areas such as patient rooms or surgical rooms where there is high throughput or demand. Moreover, this approach may be significantly faster than using a comparable portable size dehumidifier. In one example embodiment, the filter medium 132 may include glass beads or pellets which are coated with $MnO_2$, although other suitable styles of filters may also be used, and different chemicals or materials may be used for the filter medium 132 depending upon the given chemical solution that is to be used in the treatment cycle.

In accordance with another advantageous aspect, the fogging device 31 may wirelessly interface with an HVAC system in the building (e.g., such as through a wireless thermostat that has Wi-Fi connectivity, etc.). As a result, the fogging device 31 may control when the HVAC system turns on/off during/after a treatment cycle.

It should be noted that, while various features discussed above are presented individually with respect to different diagrams for clarity of illustration, these features may be combined in a same embodiment in different applications. For example, some or all of the humidity sensor 120, dehumidifier 121, and filter 130 (and/or humidifier) may be used in a same embodiment. Moreover, both time-based treatment cycles and humidity-based treatment cycles may be supported simultaneously. That is, if the humidity sensor 120 is not present in the treatment area, then treatment times may be calculated and used for the fogging device(s) 31, but otherwise the humidity sensor may be used to determine when to start and/or stop the fogging cycle. Furthermore, the treatment times for the fogging device(s) 31 may still be determined even when the humidity sensor 120 is present, in the event that the humidity sensor fails, etc., and the fogging cycle may then be concluded based upon the first processor 37 of the second processor 62 keeping the fogging time as a backup, for example.

Figure 17:
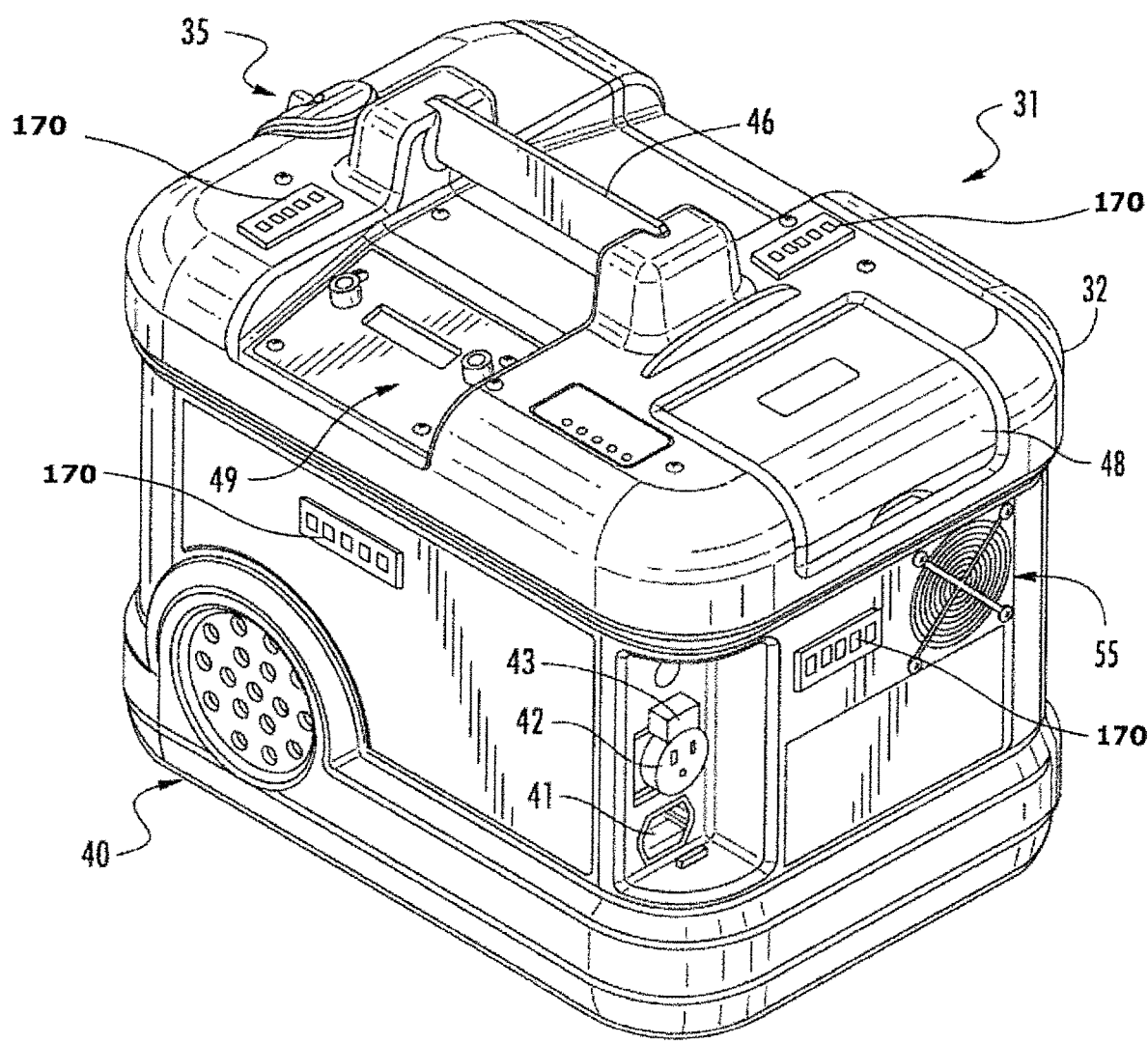
FIG. 17 is a perspective view of another embodiment of the fogging device of FIG. 1 including integrated ultraviolet (UV) lighting which is selectively activated during a fogging treatment cycle.
Figure 18:
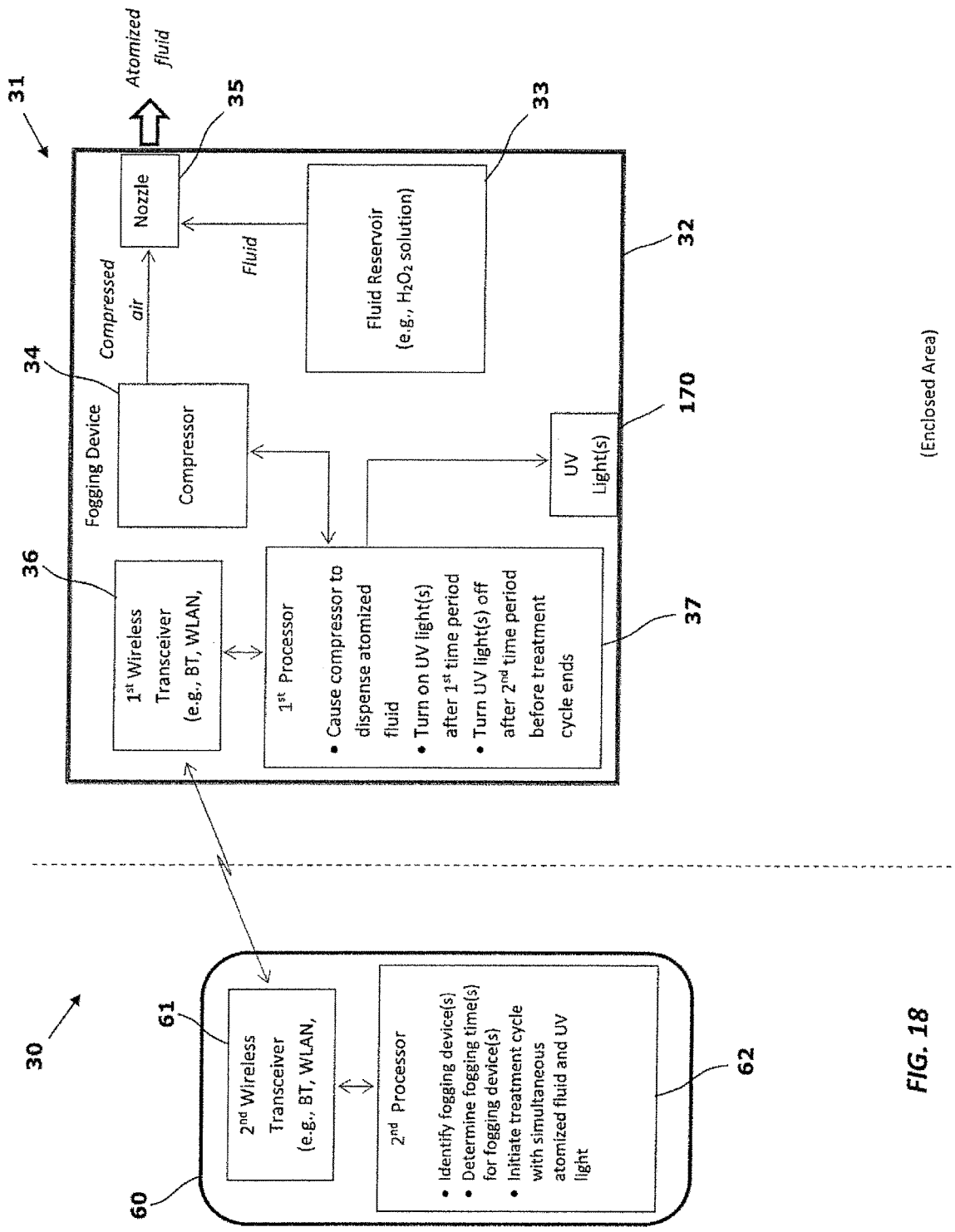
FIG. 18 is a schematic block diagram illustrating an example system including the fogging device of FIG. 17 for treating an enclosed area with an atomized disinfectant and ultraviolet light in accordance with another example embodiment.
Figure 19:
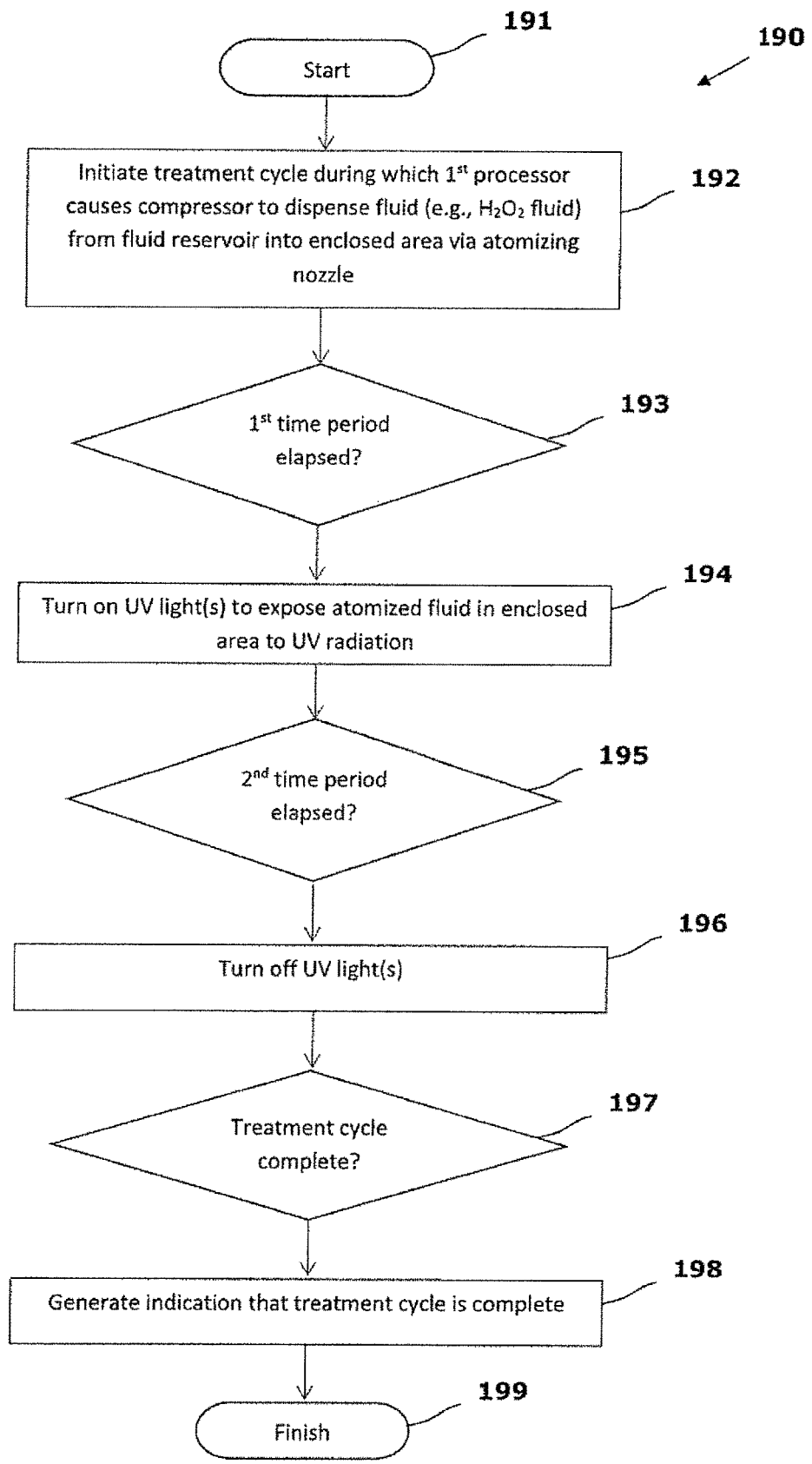
FIG. 19 is a flow diagram illustrating method aspects associated with the foggers and systems of FIGS. 18-19 and 20-21.

Turning now to FIGS. 17-19, in accordance with another example embodiment, the fogging device(s) 31 may further include a plurality of ultraviolet (UV) lights 170, which in the illustrated example are strips of light emitting diode (LED) UV lights which are coupled to or integrated with the housing 32. In the present example, the UV lights 170 are positioned on the top and sides of the housing to shine UV light in all directions around the fogging device 31, although in other embodiments the lights do not have to be on every side of the housing.

Generally speaking, certain higher wavelengths of UV light act as a natural disinfectant by penetrating the outer cell wall and cell body of microorganisms to alter their deoxyribonucleic acid (DNA), and thereby destroy the microorganisms. In this regard, certain UV light devices are sometimes used to irradiate surfaces or treatment areas for disinfection purposes. However, in addition to the ability of UV light to break down microorganisms on its own, when used in the presence of water, other lower wavelengths of UV light generate hydroxyl (.OH) free radicals. Thus, by activating the UV lights 170 during the treatment cycle when there is atomized disinfectant within the enclosed treatment area, Applicant theorizes without wishing to be bound thereto that there is a combined or compounded effect which causes organic molecules and microorganisms to be destroyed faster. That is, the pathogens are killed by one or more of: (a) the disinfectant (e.g., $H_2O_2$) in the atomized fluid; (b) the natural cell destroying power of the relatively higher UV wavelengths by themselves; and (c) the lower UV wavelengths causing the water within the atomizing fluid to produce very reactive hydroxyl free radicals which also attack molecules in microorganisms. This, in turn, may result in a significant decrease in the amount of time required to obtain a kill for any given pathogen, which may be particularly important in environments such as hospitals, etc., where rooms need to be disinfected and put back into service quickly.

Yet, UV light is also harmful to human cells for the same reasons, and it is accordingly important that operators of the fogging device 31 or others be exposed to the UV light as little as possible. As such, referring to the flow diagram 190 of FIG. 19, beginning at Block 191, the processor 37 (either responsive to the second processor 62 or via direct user input at the fogging device 31) initiates the treatment cycle as described above, at Block 192, during which the disinfectant fluid is dispensed from the fluid reservoir 33 into the enclosed area via the atomizing nozzle 35. However, the processor 37 may advantageously wait for a first time period (e.g., 30 seconds to a few minutes) and then turn on the UV lights 170 to expose the atomized fluid in the enclosed area to UV radiation (Blocks 193-194). This first time period or delay advantageously allows the operator time to exit the enclosed area before the UV lights 170 are activated. In this regard, a delay (of the same or different duration) may also be used in some embodiments from the time the operator initiates the treatment process until the time that fogging commences.

The processor 37 may further determine when a second time period has elapsed, at Block 195. In accordance with one example, the second time period may be set to coincide with the end of the dwell period (i.e., the end of the dwell period is also the end of the second time period). In this way, the UV lights 170 are activated only while atomized fluid is being dispensed. In other embodiments, the second time period may end earlier or later (e.g., part way through the dissipation phase). In any event, the second time period will generally be selected so that the UV lights 170 are turned off (Block 196) prior to the treatment cycle being fully completed. That is, the UV lights 170 may be turned off prior to providing an indication that the treatment cycle has been completed. Thus, if following proper safety precautions and waiting until the treatment cycle completion indication is provided, the operator will at no time be exposed to UV light when setting up or retrieving the fogging device(s) 31 from the treatment area. The method of FIG. 19 illustratively concludes at Block 199.

Figure 20:
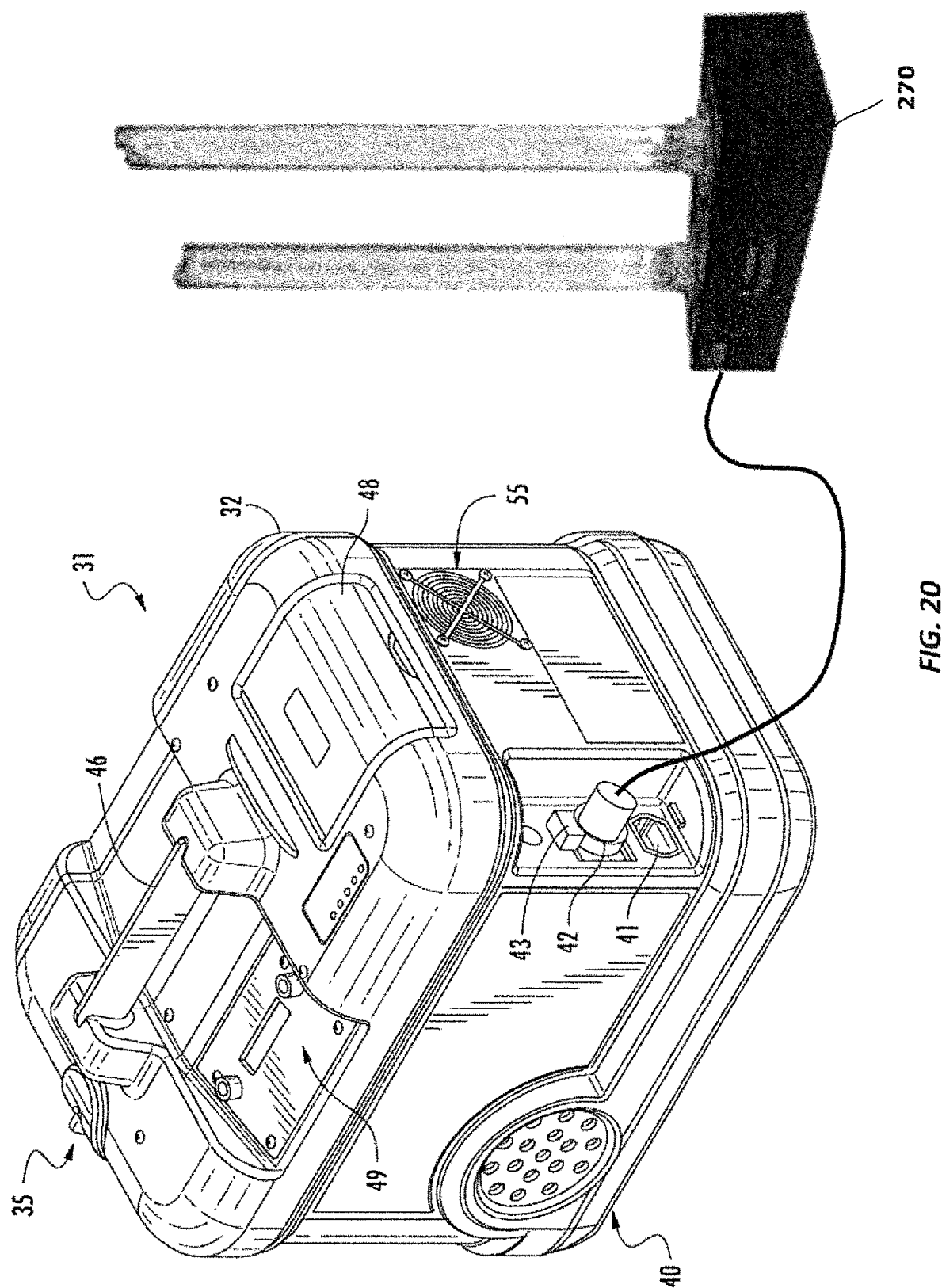
FIG. 20 is a perspective view of another example embodiment of the fogging device of FIG. 1 for selectively activating an external UV light during a fogging treatment cycle.
Figure 21:
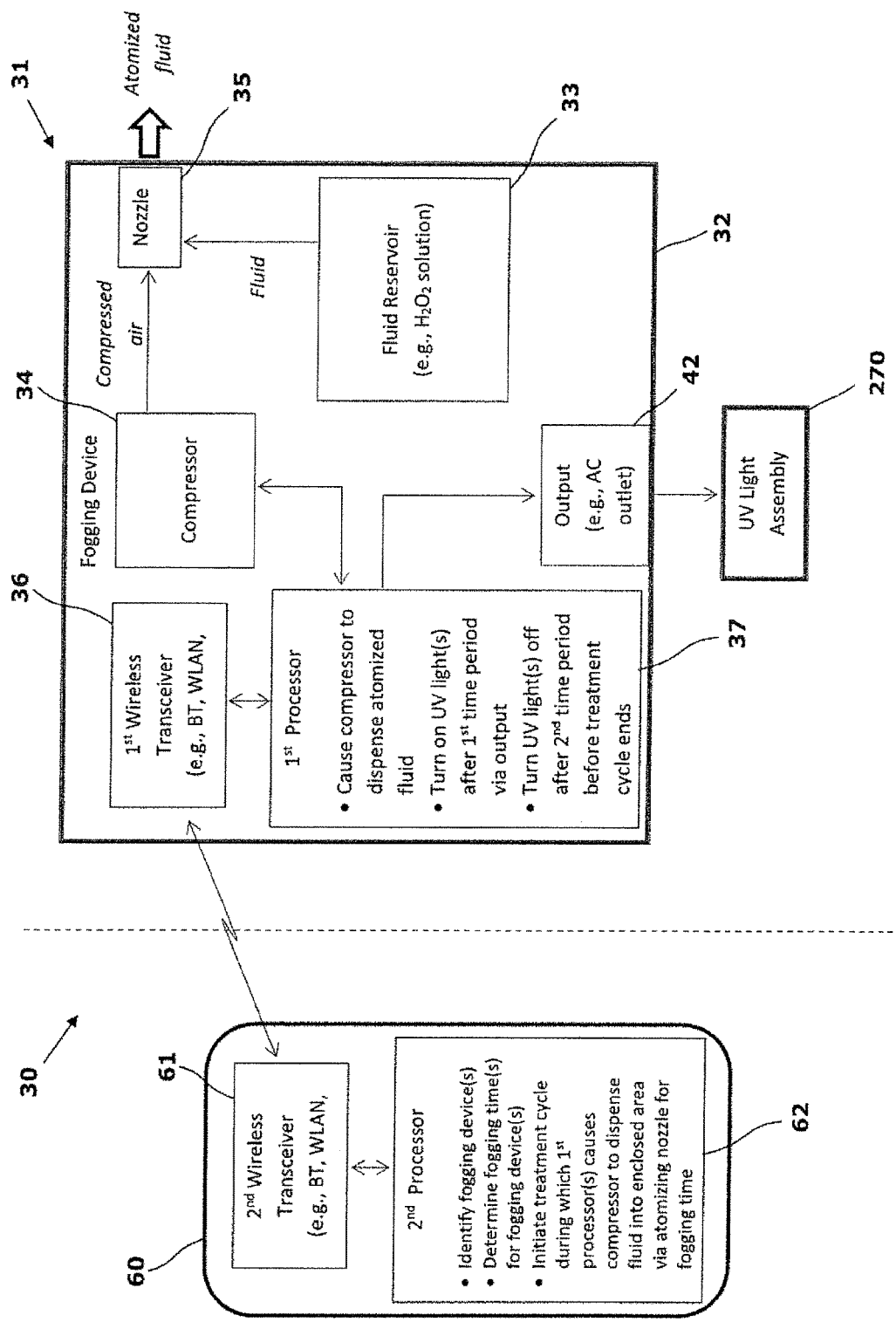
FIG. 21 is a schematic block diagram illustrating an example system including the fogging device of FIG. 20 for treating an enclosed area with an atomized disinfectant and ultraviolet light in accordance with another example embodiment.

Referring additionally to FIGS. 20-21, in accordance with another example embodiment an external UV light assembly 270 is used instead of the integrated UV lights 170 described above (although in some embodiments both may be used). In this configuration, the UV light assembly 270 is coupled to and controlled by the output 42 of the fogging device, which in this example is an AC outlet that is selectively powered by the first processor 37 to turn the UV light assembly on and off as described above with reference to FIG. 19. It should be noted that in other embodiments, the UV assembly 270 may be powered by a different source and merely controlled via the output 42 (e.g., a wireless interface, for example). Other suitable approaches for powering and controlling the UV light assembly 270 may also be used. In the illustrated example, the UV light assembly 270 includes low-pressure mercury discharge lamps, although other suitable UV light sources (or combinations thereof) may also be used in different embodiments (e.g., black lights, halogen lights, fluorescent and incandescent sources, and certain types of lasers).

Many modifications and other embodiments of the invention will come to the mind of one skilled in the art having the benefit of the teachings presented in the foregoing descriptions and the associated drawings. Therefore, it is understood that the disclosure is not to be limited to the specific embodiments disclosed, and that modifications and embodiments are intended to be included.

That which is claimed is:

1. A system for disinfecting an enclosed area comprising:
   at least one ultraviolet (UV) light; and
   a fogging device comprising
      a portable housing,
      an atomizing disinfectant generator carried by the portable housing,
      an output circuit carried by the portable housing, and
      a processor carried by the portable housing and configured to
         initiate a disinfection cycle during which the atomizing disinfectant generator dispenses atomized disinfectant fluid into the enclosed area, the disinfection cycle including a saturation phase wherein the atomizing disinfectant generator operates to dispense atomized disinfectant fluid continuously to bring the enclosed area to a target saturation level and a pulse phase wherein the atomizing disinfectant generator operates to intermittently dispense atomized disinfectant fluid to maintain the enclosed area at the target saturation level,
         after a first time period, activate the at least one UV light via the output circuit to irradiate the enclosed area and atomized disinfectant while the atomized disinfectant fluid is being dispensed into the enclosed area, and
         after a second time period later than the first time period, deactivate the at least one UV light via the output circuit and prior to completion of the disinfection cycle.

2. The system of claim 1 wherein the at least one UV light is carried by the portable housing.

3. The system of claim 1 wherein the portable housing comprises a plurality of sides and a top; and
   wherein the at least one UV light comprises a plurality of UV strip lights carried by the sides and top of the portable housing.

4. The system of claim 1 wherein the fogging device further comprises a power outlet carried by the portable housing and coupled to the output circuit; and wherein the processor activates the at least one UV light via the output circuit and the power outlet.

5. The system of claim 1 wherein the output circuit comprises a wireless communications transceiver.

6. The system of claim 1 wherein the disinfectant fluid comprises hydrogen peroxide.

7. The system of claim 1 wherein the atomizing disinfectant generator comprises:
   a disinfectant fluid reservoir for holding the disinfectant fluid;
   a compressor; and
   an atomizing nozzle coupled to the disinfectant fluid reservoir and the compressor.

8. The system of claim 1 wherein the fogging device further comprises a first wireless transceiver carried by the portable housing and coupled to the processor;
   and further comprising a wireless communications device comprising a second wireless transceiver configured to remotely communicate with the processor of the fogging device and cause the processor to initiate the treatment cycle.

9. A fogging device comprising:
   a portable housing;
   an atomizing disinfectant generator carried by the portable housing;
   an output circuit carried by the portable housing; and
   a processor carried by the portable housing and configured to
      initiate a disinfection cycle during which the atomizing disinfectant generator dispenses atomized disinfectant fluid into the enclosed area, the disinfection cycle including a saturation phase wherein the atomizing disinfectant generator operates to dispense atomized disinfectant fluid continuously to bring the enclosed area to a target saturation level and a pulse phase wherein the atomizing disinfectant generator operates to intermittently dispense atomized disinfectant fluid to maintain the enclosed area at the target saturation level,
      after a first time period, activate at least one ultraviolet (UV) light via the output circuit to irradiate the enclosed area and atomized disinfectant while the atomized disinfectant fluid is being dispensed into the enclosed area, and
      after a second time period later than the first time period, deactivate the at least one UV light via the output circuit and prior to completion of the disinfection cycle.

10. The fogging device of claim 9 wherein the at least one UV light is carried by the portable housing.

11. The fogging device of claim 9 wherein the portable housing comprises a plurality of sides and a top;
    and wherein the at least one UV light comprises a plurality of UV strip lights carried by the sides and top of the portable housing.

12. The fogging device of claim 9 further comprising a power outlet carried by the portable housing and coupled to the output circuit; and wherein the processor activates the at least one UV light via the output circuit and the power outlet.

13. The fogging device of claim 9 wherein the output circuit comprises a wireless transceiver.

14. A method for disinfecting an enclosed area using a fogging device and at least one ultraviolet (UV) light, the fogging device comprising a portable housing, an output circuit carried by the portable housing, and an atomizing disinfectant generator carried by the portable housing, the method comprising:
    initiating a disinfection cycle during which the atomizing disinfectant generator dispenses atomized disinfectant fluid into the enclosed area, the disinfection cycle including a saturation phase wherein the atomizing disinfectant generator operates to dispense atomized disinfectant fluid continuously to bring the enclosed area to a target saturation level and a pulse phase wherein the atomizing disinfectant generator operates to intermittently dispense atomized disinfectant fluid to maintain the enclosed area at the target saturation level;

after a first time period, activating the at least one UV light via the output circuit to irradiate the enclosed area and atomized disinfectant from the fogging device while the atomized disinfectant fluid is being dispensed into the enclosed area; and after a second time period later than the first time period, deactivating the at least one UV light via the output circuit from the fogging device and prior to completion of the disinfection cycle.

15. The method claim 14 wherein the at least one UV light is carried by the portable housing.

16. The method claim 14 wherein the portable housing comprises a plurality of sides and a top; and wherein the at least one UV light comprises a plurality of UV strip lights carried by the sides and top of the portable housing.

17. The method claim 14 wherein the fogging device further comprises a power outlet carried by the portable housing and coupled to the output circuit; and wherein activating comprises activating the at least one UV light via the output circuit and the power outlet.

* * * * *